(12) United States Patent
Stalford

(10) Patent No.: US 10,059,582 B2
(45) Date of Patent: *Aug. 28, 2018

(54) THREE DIMENSIONAL (3D) ROBOTIC MICRO ELECTRO MECHANICAL SYSTEMS (MEMS) ARM AND SYSTEM

(71) Applicant: Harold L. Stalford, Norman, OK (US)

(72) Inventor: Harold L. Stalford, Norman, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 15/295,604

(22) Filed: Oct. 17, 2016

(65) Prior Publication Data

US 2017/0129770 A1 May 11, 2017

Related U.S. Application Data

(63) Continuation of application No. 14/247,021, filed on Apr. 7, 2014, now Pat. No. 9,473,048, which is a (Continued)

(51) Int. Cl.
*B81B 5/00* (2006.01)
*H02N 11/00* (2006.01)
(Continued)

(52) U.S. Cl.
CPC ............... *B81B 5/00* (2013.01); *A61B 10/02* (2013.01); *A61B 17/285* (2013.01); *A61B 18/24* (2013.01);
(Continued)

(58) Field of Classification Search
CPC ........... B81B 5/00; A61B 34/30; A61B 34/72; A61B 10/02; A61B 17/285; A61B 18/24;
(Continued)

(56) References Cited

U.S. PATENT DOCUMENTS

| | | |
|---|---|---|
| 2,998,805 A | 9/1961 | Usab |
| 3,136,891 A | 6/1964 | Graftieaux et al. |

(Continued)

FOREIGN PATENT DOCUMENTS

| | | |
|---|---|---|
| DE | 10 2005 010 279 A1 | 9/2006 |
| EP | 472150 A2 | 2/1992 |

(Continued)

OTHER PUBLICATIONS

Allen, James J. et al., "Micromachine Wedge Stepping Motor", Sandia National Laboratories, Intelligent Micromachine Dept., 1998 ASME International Mechanical Engineering Congress and Exposition, Anaheim, CA, Nov. 15-20, 1998. (6 pages).

(Continued)

*Primary Examiner* — Michelle Lopez
(74) *Attorney, Agent, or Firm* — Fish & Richardson P.C.

(57) ABSTRACT

A micro assembly having a substrate and an operating plane coupled to the substrate. The operating plane is movable from an in-plane position to an out-of-plane position. One or more electric connections provide electric power from the substrate to the operating plane in the out-of-plane position. A tool is coupled to the operating plane. The tool is operable to receive electric power from the operating plane to perform work.

12 Claims, 60 Drawing Sheets

Related U.S. Application Data continuation of application No. 13/406,454, filed on Feb. 27, 2012, now Pat. No. 8,689,899, which is a continuation of application No. 12/470,474, filed on May 21, 2009, now Pat. No. 8,122,973.

(60) Provisional application No. 61/055,038, filed on May 21, 2008.

(51) Int. Cl.
| | | |
|---|---|---|
| *H02N 10/00* | (2006.01) | |
| *B81B 7/02* | (2006.01) | |
| *A61B 34/30* | (2016.01) | |
| *A61B 34/00* | (2016.01) | |
| *A61B 10/02* | (2006.01) | |
| *A61B 18/24* | (2006.01) | |
| *A61B 17/285* | (2006.01) | |
| *A61B 17/29* | (2006.01) | |
| *A61B 17/00* | (2006.01) | |

(52) U.S. Cl.
CPC .............. *A61B 34/30* (2016.02); *A61B 34/72* (2016.02); *B81B 7/02* (2013.01); *H02N 10/00* (2013.01); *H02N 11/006* (2013.01); *A61B 2017/00345* (2013.01); *A61B 2017/2932* (2013.01)

(58) Field of Classification Search
CPC ............ A61B 7/02; A61B 2017/00345; A61B 2017/2932; H02N 10/00; H02N 11/006
USPC .......................................... 173/152; 310/306
See application file for complete search history.

(56) References Cited

U.S. PATENT DOCUMENTS

| | | | |
|---|---|---|---|
| 3,650,033 A | 3/1972 | Behne et al. | |
| 4,139,167 A | 2/1979 | Osanai | |
| 4,323,805 A | 4/1982 | Caby et al. | |
| 4,426,158 A | 1/1984 | Müller et al. | |
| 4,518,182 A | 5/1985 | Cousin et al. | |
| 5,189,323 A | 2/1993 | Carr et al. | |
| 5,254,893 A | 10/1993 | Ide | |
| 5,296,775 A | 3/1994 | Cronin et al. | |
| 5,449,493 A | 9/1995 | Rokugawa | |
| 5,631,514 A | 5/1997 | Garcia et al. | |
| 5,677,579 A | 10/1997 | Dona et al. | |
| 5,710,466 A | 1/1998 | Allen et al. | |
| 5,780,288 A | 7/1998 | Rohwer | |
| 5,874,798 A | 2/1999 | Wiegele et al. | |
| 5,959,376 A * | 9/1999 | Allen ................. | F16H 27/02 |
| | | | 310/306 |
| 6,121,553 A | 9/2000 | Shinada et al. | |
| 6,175,170 B1 | 1/2001 | Kota et al. | |
| 6,179,596 B1 | 1/2001 | Weisener et al. | |
| 6,211,599 B1 | 4/2001 | Barnes et al. | |
| 6,240,312 B1 | 5/2001 | Alfano et al. | |
| 6,313,562 B1 | 11/2001 | Barnes et al. | |
| 6,366,186 B1 | 4/2002 | Hill et al. | |
| 6,392,313 B1 | 5/2002 | Epstein et al. | |
| 6,422,011 B1 | 7/2002 | Sinclair | |
| 6,616,326 B2 | 9/2003 | White | |
| 6,655,964 B2 | 12/2003 | Fork et al. | |
| 6,848,175 B2 | 2/2005 | Fork et al. | |
| 6,903,861 B1 | 6/2005 | Allen | |
| 6,922,327 B2 | 7/2005 | Chua et al. | |
| 6,973,365 B1 | 12/2005 | Mercanzini | |
| 6,979,936 B1 | 12/2005 | Ganor et al. | |
| 7,018,575 B2 | 3/2006 | Brewer et al. | |
| 7,025,619 B2 | 4/2006 | Tsui et al. | |
| 7,036,769 B2 * | 5/2006 | Wood ................. | B64C 33/02 |
| | | | 244/11 |
| 7,044,653 B2 | 5/2006 | Reis | |
| 7,096,568 B1 | 8/2006 | Nilsen et al. | |
| 7,109,638 B2 | 9/2006 | Kitahara et al. | |
| 7,159,842 B1 | 1/2007 | Taylor et al. | |
| 7,196,454 B2 | 3/2007 | Baur et al. | |
| 7,201,185 B2 | 4/2007 | Poppe et al. | |
| 7,220,973 B2 | 5/2007 | Yu et al. | |
| 7,378,777 B2 * | 5/2008 | Moteki ............... | H01L 41/0913 |
| | | | 310/323.02 |
| 7,423,364 B2 | 9/2008 | Williams et al. | |
| 7,505,373 B2 | 3/2009 | Paratte et al. | |
| 7,636,277 B2 | 12/2009 | Minotti et al. | |
| 7,698,818 B2 | 4/2010 | Voegele et al. | |
| 8,122,973 B2 * | 2/2012 | Stalford ............... | B81C 99/002 |
| | | | 173/152 |
| 8,134,276 B2 | 3/2012 | Stalford | |
| 8,159,107 B2 * | 4/2012 | Stalford ............... | B81B 3/0024 |
| | | | 310/306 |
| 9,473,048 B2 * | 10/2016 | Stalford ............... | B81C 99/002 |
| 2002/0041729 A1 | 4/2002 | Mastromatteo et al. | |
| 2002/0181886 A1 | 12/2002 | Fischer et al. | |
| 2003/0024963 A1 | 2/2003 | Fujii et al. | |
| 2003/0099763 A1 | 5/2003 | Sandhage | |
| 2003/0183008 A1 | 10/2003 | Bang et al. | |
| 2004/0119354 A1 | 6/2004 | Takada et al. | |
| 2004/0126254 A1 | 7/2004 | Chen et al. | |
| 2005/0006982 A1 | 1/2005 | Williams et al. | |
| 2005/0025643 A1 | 2/2005 | Lin | |
| 2005/0082950 A1 | 4/2005 | Zakoji | |
| 2005/0270135 A1 | 12/2005 | Chua et al. | |
| 2006/0042381 A1 | 3/2006 | Still | |
| 2006/0098047 A1 | 5/2006 | Silverbrook | |
| 2006/0211761 A1 | 9/2006 | Kumar et al. | |
| 2006/0228094 A1 | 10/2006 | Alasaarela et al. | |
| 2006/0234412 A1 | 10/2006 | Lazaroff | |
| 2007/0087474 A1 | 4/2007 | Eklund et al. | |
| 2007/0103029 A1 | 5/2007 | Fedder et al. | |
| 2007/0103264 A1 | 5/2007 | Yang | |
| 2008/0048519 A1 | 2/2008 | Stalford | |
| 2012/0167377 A1 | 7/2012 | Stalford | |
| 2013/0005955 A1 | 1/2013 | Stalford | |

FOREIGN PATENT DOCUMENTS

| | | |
|---|---|---|
| GB | 1388119 A | 3/1975 |
| JP | 03292690 A | 12/1991 |
| JP | 2001148461 A | 5/2001 |
| JP | 2003120663 A | 4/2003 |
| JP | 2003148661 A | 4/2003 |
| WO | WO 007/143623 | 12/2007 |

OTHER PUBLICATIONS

Andersson, Helene, van den Berg, Albert, "Microfluidic devices for cellomics: a review", copyright 2003 Elsevier Science, (11 pages), <http://bios.ewi.utwente.nl/publications/bios/20003/pdffiles2003/Microfluidicdevicesforcellomics>.

Barnes, Stephen M., et al., "Torsional Ratcheting Actuating System", Sandia National Laboratories, Albuquerque, NM, Technical Proceedings of the 2000 International Conference on Modeling and Simulation of Microsystems, Chapter 6: Characterization, Parameter Extraction, Calibration, Mar. 27-29, 2000, pp. 273-276.

Conference Proceedings entitled "12th International Congress of Biorheology and 5th International Conference on Clinical Hemorheology", Chongquig, China, May 30, 2005-Jun. 3, 2005, Scientific Program, copyright 2005—IOS Press, Biorheology 42, (14 pages).

Cusin, P., "Compact and precise positioner based on the Inchworm principal", Faculty of Science and Engineering, Ritsumeikan University, Kusatsu, Shiga, Japan, J. Micromech. Microeng. vol. 10, 2000, received Apr. 18, 2000. pp. 516-521.

Dagel, D.J., et al., "Out-of-plane, rotary micromirrors for reconfigurable photonic applications", Sandia National Laboratories, Albuquerque, NM, Proceedings of SPIE vol. 4983, Pub. 2003, pp. 114-121.

DENSO Micro-Car, DENSO North America, from the Guinness World Record. Internet: <http://www.densocorp-na.com/corporate/gwr.html> (2 pages)—date unknown.

(56) References Cited

OTHER PUBLICATIONS

"DNM—Do-Nothing Machine" located at <http://www.folktoys.com/atmechanical.htm>—date unknown.

Fischer, Kayte, "Batteries Not Included, Big Steps in Small-Scale Energy Sources", Berkeley Science Review, Issue 12, pp. 25-28. <http://sciencereview.berkeley.edu/articles/issue12/smallenergy.pdf>.

Fukushige, T., et al., "Large-output-force out-of-plane MEMS actuator array", Proceedings of SPIE International Symposium on Microelectronics, MEMS, and Nanotechnology, The University of western Australia, Perth, Australia, Dec. 9-12, 2003 (10 pages).

Ho Nam Kwon, et al., "Characterization of a Micromachined Inchworm Motor with Thermoelastic Linkage Actuators", Dept. of Mechatronics, K-JIST, Gwangju, Korea, IEEE, 2002, pp. 586-589.

Ide, Russell D., Abstract entitled "Shaft Support Assembly for Use in a Polygon Mirror Drive Motor", from U.S. Pat. No. 5,254,893 issued Oct. 19, 2007(2 pages).

Integrated MicroElectroMechanical Technologies; printed May 14, 2007 from website http://mems.sandia.gov/about/electro-mechanical.html; (3 pages).

Keating, D.J., et al., "Numerical Simulation of Micro-Assembly of MEMS Devices and Post Assembly Electromechanical Actuation", IntelliSuite User's Manual, IntelliSense Corporation, 1999 (8 pages).

Kolesar, Ed, Lecture Notes entitled "Introduction to Microeletromechanical Systems (MEMS)—Lecture 1 Topics", Texas Christian University, Department of Engineering, (approx. May through Aug. 2005), 18 pages.

Kolesar, Ed, Lecture Notes entitled "Introduction to Microeletromechanical Systems (MEMS)—Lecture 2 Topics", Texas Christian University, Department of Engineering, (approx. May through Aug. 2005), 17 pages.

Konishi, Satoshi, et al., "Electrostatically Controlled Linear Inchworm Actuator for Precise Step and Parallel Motion", Ritsumeikan University, IEEJ Trans. IA, vol. 126, No. 10, 2006. pp. 1325-1329, with Extended Summary.

Lai, Yen-Jyh, et al., "Out-of-Plane MEMS Shutter with Continuous Motion Capability for VOA Application", Asia Pacific Microsystems, Inc., No. 2, R&D Road VI, Science-Based Industrial Park, Hsinchu, Taiwan, Ref. W11-(15)-1, (p. 141)—date unknown.

Last, M., Subramaniam V., K.S.J. Pister, "Out-of-Plane Motion of Assembled Microstructures Using a Single Mask SOI Process", Transducers, Seoul, Korea, Jun. 5-9, 2005 (4 pages).

Last, M.E., "Silicon-on-Insulator Microassembly", dissertation talk Dec. 2005 (40 pages) <http://www.bsac.eecs.berkeley.edu/~mattlast/papers>>.

Last, Matthew Emanuel, Ph.D. Dissertation entitled "Pick and Place Silicon on Insulator Microassembly", UC Berkely, Electrical Engineering and Computer Sciences, Fall 2005 (179 pages).

Legtenberg, Rob et al. "Electrostatic Microactuators with Integrated Gear Linkages for Mechanical Power Transmission", In: MEMS '96, Proceedings 'An Investigation of Micro Structures, Sensors, Actuators, Machines and Systems', IEEE, The Ninth Annual International Workshop on Feb. 11-15, 1996, pp. 204-209.

Mani, S.S., Presentation entitled "Notes—MEMS: Micro Electro Mechanical System", Sandia National Laboratories, copyright 2000,(11 pages)—date unknown.

MicroTAS2003 Program from the Transducer Research Foundation, dated Oct. 5, 2003 through Oct. 9, 2003 in Lake Tahoe, Nevada, (31 pages); <www.transducer-research-foundation.org/microtas2003/program/MicroTAS2003_Program.pdf>.

Milanovic, V., Last, M., Pister, K.S.J., "Laterally Actuated Torsional Micromirrors for Large Static Deflection", Photonics Technology Letters, vol. 15, No. 2, Feb. 2003, pp. 245-247.

Milanovic, Velijko, Last, Matthew, Pister, Kristofer S.J., "Torsional Micromirrors with Lateral Actuators", Transducers 01, Muenchen, Germany, Jun. 2001 (4 pages).

Nguyen, H. et al., "Device Transplant of Optical MEMS for Out of Plane Beam Steering", Dept. of Electrical Engineering, University of California at Los Angeles, Ref. 0-7803-5998-4/01, 2001, pp. 325-328.

Nnebe, Chukwuney Stanley, Abstract entitled: "A Mechanically-raised Micromachined Variable Inductor Coil", Cornell University, May 19, 1999, (1 page).

Okandan, Dr. Murat, "Track 3—Therapeutic Micro/Nanotechnology", BioMEMS and Biomedical Nanotechnology World, 2002 (3 pages).

Okandan, M., et al., "Development of Surface Micromachining Technologies for Microfluidics and BioMEMS", Sandia National Laboratories, Albuquerque, NM,Proc. SPIE vol. 4560, pp. 133-139, Microfluidics and BioMEMS, Carlos H. Mastrangelo; Holger Becker; Eds., Sep. 2001.

Pister, Prof. Kris, "Overview of Pistertrans", Univ. of California, Berkeley, CA, National Workshop on Future Sensing Systems, Lake Tahoe, Granlibakken Conference Center, Aug. 26-28, 2002, (7 pages) <www.ce.berkeley.edu/sensors/transcripts/Monday/Pistertrans.pdf>.

Popa, D.O. and Stephanou, H.E., "Micro and Meso Scale Robotic Assembly", SME Journal of Manufacturing Processes, vol. 6, No. 1, 2004, pp. 52-71.

Rodgers, M. Steven, et al., "Designing and Operating Electrostatically Driven Microengines",Sandia National Laboratories, Albuquerque, NM, SAND-98-0493C, Mar. 9, 1998, (10 pages).

Romig, Jr., Dr. A.D., Presentation entitled "Mitigating the Chemical, Biological, Radiological and Nuclear (CBRN) Threat", presented to ASM, International, Albuquerque Chapter, Sandia National Laboratories, Sep. 29, 2004, (30 pages).

Sandia document entitled: "Introduction and Review of Fabrication Concepts", copyright 2002 Sandia National Laboratories (Need Date), (37 pages).

Sandia document entitled: "MEMS Bibliography—Actuators: SUMMiT V Technology", copyright 2005 Sandia National Laboratories, (4 pages) <http://mems.sandia.gov/tech-info/mems-bib-actuators.html>.

Sandia document entitled: "Pac-Man-like microstructure interacts with red blood cells", News Releases, Sandia National Laboratories, Aug. 15, 2001, internet: <http://www.sandia.gov/media/NewsRel/NR2001/gobbler.htm> (4 pages).

Sandia document entitled: "Sandia's new 'inchworm' actuator studies friction at the microscale, provides detailed information" from Labnews at Sandia Laboratories, Albuquerque, NM, Feb. 20, 2004, (11 pages).

Sandison, David R., Presentation entitled "Moving MEMS from Novelty to Necessity—A National Security Perspective", Sandia National Laboratories, Albuquerque, NM, MEMS Technologies, Jul. 27, 2006 (34 pages).

Sasaki, H. et al., "A Novel Type of Mechanical Power Transmission Array for Switching Densely-Arrayed Actuator Systems", Dept. of Micro System Eng., Nagoya University, Nagoya, Japan, MEMS 2006, Istanbul, Turkey, Jan. 22-26, 2006. pp. 790-793.

Schurr, Prof. Dr. Marc O. , Presentation for the VECTOR consortium entitled "Microrobotics and allied technologies in medicine: key enablers of prevention and early treatment of diseases", Novineon Healthcare Technology Partners GmbH, Brussels, Feb. 12, 2007. (30 pages).

Sexton, Fred W., Presentation entitled "Adhesion & Friction Issues in Contacting Microsystems", Radiation & Reliability Physics Dept., Sandia National Laboratories, Sematech SRC, Oct. 25-27, 2004 (25 pages).

Sniegowski, J.J. et al., "An Application of Mechanical Leverage to Microactuation", 8th International Conference on Solid State Sensors and Actuators, and Eurosensors IX, Proc. Transducers '95 Eurosensors IS, Stockholm, Sweden, Jun. 25-29, 1995, vol. 2, pp. 364-367.

Stalford, Prof. Harold L., Presentation entitled "Novel Microblender for Lysing Cells and Other Microfluidic Applications", School of Aerospace and Mechanical Engineering, University of Oklahoma, 12th Intrnl. Congress of Biorheology (ICB) and the 5th Intrnl. Conf.

(56) References Cited

OTHER PUBLICATIONS on Clinical Hemorheology (ICCH), May 30-Jun. 3, 2005 (Disclosed during presentation on Jun. 2, 2005), Chongquing, China, (28 pages).
Szabo, F.R. and Kladitis, P.E., "Design, Modeling and Testing of Polysilicon Optothermal Actuators for Power Scavenging Wireless Microrobots", MEMS, NANO and Smart Systems, ICMENS 2004, Proceedings of International Conference on Aug. 25-27, 2004, pp. 446-452.
Tanke, Matt, et all., Microelectronics course overview entitled "Measuring Cell Adhesion Using MEMS Technology", ME 381, Northwestern University, Fall 2006, taught by Prof. Horacia D. Espinosa (21 pages).
Trease, B.P. et al., "Design and Analysis of an Out-of-Plane Micro Thermal Actuator", IMECE2003_41393, International mechanical engineering Congress and Exposition, Nov. 15-21, 2003, Washington, D.C., (3 pages).
Yang, E.H., et al., "Design and Fabrication of a Large Vertical Travel Silicon Inchworm Microactuator for the Advanced Segmented Silicon Space Telescope", Jet Propulsion Laboratory, Calif. Inst. of Technology, Pasadena, CA., Proceedings of SPIE—vol. 4981, MEMS Components and Applications for Industry, Automobiles, Aerospace, and Communication II, Siegfried W. Janson, Editor, Jan. 2003, pp. 107-112.
Yeh, Richard, Hollar, Seth, and Pister, Kristofer S. J., "Single Mask, Large Force, and Large Displacement Electrostatic Linear Inchworm Motors", Berkeley Sensor and Actuator Center, Dept. of Electrical Engineering and Computer Science, Univ. of California, Berkeley, CA, Journal of Microelectromechanical Systems, vol. 11, No. 4, Aug. 2002, pp. 330-336.
Zickar, Michael et al., "Quasi-dry Release for Micro Electro-Mechanical Systems", University of Neuchatel, IMT, SAMLAB, Jaquet-Droz 1, 2007 Neuchatel, Switzerland (6 pages).
Specification of U.S. Appl. No. 11/757,313, filed Jun. 1, 2007, entitled Met hods and Systems for Micro Machines (71 pages).
Specification of U.S. Appl. No. 11/757,321, filed Jun. 1, 2007, entitled Methods and Systems for Micro Transmissions (68 pages).
Specification of U.S. Appl. No. 11/757,331, filed Jun. 1, 2007, entitled Micro Rotary Machine and Methods for Using Same (69 pages).
Specification of U.S. Appl. No. 11/757,341, filed Jun. 1, 2007, entitled Micro Transport Machine and Methods for Using Same (69 pages).
Specification of U.S. Appl. No. 11/739,716, filed Apr. 25, 2007, entitled Microelectromechanical Pump Utilizing Porous Silicon (41 pages).
Specification of U.S. Appl. No. 11/746,147, filed May 9, 2007, entitled Microelectromechanical Tunable Inductor (34 pages).
Specification of U.S. Appl. No. 11/757,343, filed Jun. 1, 2007, entitled Methods and Systems for Positioning Micro Elements (69 pages).
Specification of U.S. Appl. No. 11/757,344, filed Jun. 1, 2007, entitled Methods and Systems for Micro Bearings (68 pages).
Notification of Transmittal of the International Search Report and the Written Opinion of the International Searching Authority of Application No. PCT/US2007/070359; filed Jun. 4, 2007 and dated Dec. 24, 2007—Corrected Version (10 pages).
Notification Concerning Transmittal of International preliminary Report on Patentability for PCT application No. PCT/US2007/070359 filed Jun. 4, 2007 and dated Dec. 18, 2008 (9 pages).
Final Corrected Version—International Search Report and Written Opinion of the International Searching Authority of Application No. PCT/US2007/070359; filed Jun. 4, 2007 and dated Dec. 24, 2007— (12 pages).
Caldarelli-Stefano, R., et al., Use of Magnetic Beads for Tissue DNA Extraction and IS6110 *Mycobacterium tuberculosis* PCR, J. Clin Pathol: Mol Pathol, Jan. 19999, pp. 158-166.
Carpita, Nocholas C., Tensile Strength of Cell Walls of Living Cells, Plant Physiol, vol. 79, Jun. 1985, pp. 485-488.
Choi, Jin-Woo, et al., Development and Characterization of Mcrofluidic Devices and Systems for Magnetic Bead-Based Biochemical Detection, Biomedical Microdevices, vol. 3, No. 3, (2001), pp. 191-200.
Gijs, martin A.M., Magnetic Bead Handling ON-Chip: New Opportunities for Analytical Applications, Microfluid Nanoflid, Oct. 2004; vol. 1, pp. 22-40.
Kim Changhyun and Wise, Kensall D., A 64-Site Multishank CMOS Low-Profile Neutral Stimulating Probe, IEEE J. of Solid-State Circuits, vol. 31, No. 9, Sep. 1996, pp. 1230-1238.
Kovacs, Gregory T. A., et al., Regeneration Microelectrode Array for Peripheral Nerve Recording and Stimulation, IEEE Transactions on Biomedical Engineering, vol. 39, No. 9, Sep. 1992, pp. 893-902.
Lee, H., et al., Manipulation of Biological Cells Using a Microelectromagent Matrix, Applied Physics Letters, vol. 85, No. 6, Aug. 2004, pp. 1063-1065.
Maluf, Nadim I., et al., Medical Applications of MEMS, WESCON 1995, Nov. 7-9, 1995, pp. 300-306.
Maulf, Nadim I., et al., Recent Advances in Medical Applications of MEMS, WESCON 1996, Oct. 22-24, 1996, pp. 60-63.
Mijailovich, Srboljub M., et al., A Finite Element Model of Cell Deformation During Magnetic Bead Twisting, J. Appl. Physiol, vol. 93, Jun. 2002, pp. 1429-1436.
Najafi, Khalil, Solid-State Microsensors for Cortical Nerve Recordings, IEEE Engineering in Medicine and Biology, Jun./Jul. 1994, pp. 375-387.
Rebello, Keith J., Applications of MEMS in Surgery, Proceedings of the IEEE, vol. 92, No. 1, Jan. 2004, pp. 43-55.
Regehr, Wade G., et al., A Long-Term In Vitro Silicon-Based Microelectrode-Neuron Connection, IEEE Transactions on Biomedical Engineering, vol. 35, No. 12, Dec. 1988, pp. 1023-1031.
Smith, Steven B., et al., Direct Mechanical Measurements of the Elasticity of Single DNA Molecules by Using Magnetic Beads, Science, vol. 258, Nov. 1992, pp. 1122-1126.
Office Action issued in related U.S. Appl. No. 11/757,331 dated Sep. 9, 2009; 15_ pages.
Office Action issued in related U.S. Appl. No. 11/757,331 dated Feb. 26, 2010; 7 pages.
Office Action issued in related U.S. Appl. No. 11/757,343 dated Jul. 24, 2009; 19 pages.
Office Action issued in related U.S. Appl. No. 11/757,343 dated Feb. 28, 2010; 19 pages.
Office Action issued in related U.S. Appl. No. 11/757,343 dated Sep. 9, 2010; 21 pages.
Office Action issued in related U.S. Appl. No. 11/757,344 dated Dec. 30, 2009; 18 pages.
Office Action issued in related U.S. Appl. No. 11/757,344 dated Sep. 15, 2010; 10 pages.
Office Action issued in related U.S. Appl. No. 11/757,321 dated Jan. 21, 2011; 20 pages.
Office Action issued in related U.S. Appl. No. 11/757,343 dated Jan. 6, 2011; 12 pages.
Office Action Issued in related U.S. Appl. No. 12/470,474 dated Feb. 16, 2011; 16 pages.
Office Action Issued in related U.S. Appl. No. 11/757,344 dated Jun. 9, 2011; 12 pages.
Office Action Issued in related U.S. Appl. No. 11/757,313 dated Aug. 2, 2011; 11 pages.
Advisory Action Issued in related U.S. Appl. No. 11/757,344 dated Sep. 9, 2011; 3 pages.
Office Action Issued in related U.S. Appl. No. 11/757,321 dated Oct. 20, 2011; 9 pages.
Advisory Action Issued in related U.S. Appl. No. 11/757,321 dated Jan. 3, 2012; 4 pages.
Office Action Issued in related U.S. Appl. No. 11/757,313 dated Mar. 1, 2012; 14 pages.
Office Action Issued in related U.S. Appl. No. 11/757,313 dated Sep. 14, 2012; 12 pages.
Office Action Issued in related U.S. Appl. No. 11/757,321 dated Feb. 15, 2013; 7 pages.
Office Action Issued in related U.S. Appl. No. 13/448,039 dated Feb. 26, 2013; 9 pages.

(56) References Cited

OTHER PUBLICATIONS

Office Action Issued in related U.S. Appl. No. 11/757,313 dated Mar. 26, 2013; 11 pages.
Office Action Issued in related U.S. Appl. No. 13/417,564 dated May 16, 2013; 10 pages.
Office Action Issued in related U.S. Appl. No. 11/757,321 dated Sep. 17, 2013; 11 pages.
Office Action Issued in related U.S. Appl. No. 13/448,039 dated Oct. 10, 2013; 15 pages.
Office Action issued in related U.S. Appl. No. 11/757,341 dated Oct. 10, 2013; 8 pages.
Office Action issued in related U.S. Appl. No. 13/647,218 dated Oct. 21, 2013; 10 pages.
Office Action issued in related U.S. Appl. No. 11/757,313 dated Oct. 29, 2013; 11 pages.
Office Action issued in related U.S. Appl. No. 13/417,564 dated Feb. 5, 2014; 6 pages.
Office Action issued in related U.S. Appl. No. 11/757,341 dated May 8, 2014; 7 pages.
Office Action issued in related U.S. Appl. No. 11/757,321 dated May 13, 2014; 7 pages.
Office Action issued in related U.S. Appl. No. 13/647,218 dated Jul. 17, 2014; 6 pages.
Office Action issued in related U.S. Appl. No. 13/417,564 dated Jul. 29, 2014; 12 pages.
Office Action issued in related U.S. Appl. No. 11/757,341 dated Oct. 23, 2014; 7 pages.
Office Action issued in related U.S. Appl. No. 13/417,564 dated Nov. 26, 2014; 5 pages.
Office Action issued in related U.S. Appl. No. 11/7547,341 dated Feb. 26, 2015; 7 pages.
Office Action issued in related U.S. Appl. No. 14/247,021 dated Oct. 8, 2015; 7 pages.
Office Action issued in related U.S. Appl. No. 14/247,021 dated Feb. 9, 2016; 5 pages.
Office Action issued in related U.S. Appl. No. 14/512,176 dated Jun. 1, 2015; 9 pages.

\* cited by examiner $$\mu m := 10^{-6} m \qquad \mu N := 10^{-6} N$$

MATERIAL PROPERTIES $$E_{poly} := 0.16 \, \frac{N}{\mu m^2} \qquad G_{poly} := 0.772 \, \frac{N}{\mu m^2} \qquad \nu_{poly} := 0.23$$

$$\rho_{poly} := 2.33 \cdot 10^{-12} \, \frac{gm}{\mu m^3} \qquad U_{poly} := 0.00155 \, \frac{N}{\mu m^2}$$

DIMENSIONS $$\ell_{plane} := 1000 \, \mu m \qquad w_{plane} := 500 \, \mu m \qquad t_{plane} := 11 \, \mu m$$

$$t_{P2} := 1.5 \, \mu m \qquad t_{P3} := 2.25 \, \mu m \qquad t_{P4} := t_{P3} \qquad t_{sacox} := 2 \, \mu m$$

$$t_{axis} := t_{P3} \qquad w_{axis} := 5.5 \, \mu m$$

FIG. 2A

CALCULATIONS $$W_{plane} := \ell_{plane} \cdot w_{plane} \cdot t_{plane} \cdot \rho_{poly} \cdot g \qquad W_{plane} = 0.126 \, \mu N$$

$$I_p := \frac{t_{axis} \cdot w_{axis}}{3} \cdot \left( t_{axis}^2 + w_{axis}^2 \right) \qquad I_p = 145.564 \, \mu m^4$$

TORQUE DUE TO PLATE $$cg_{plane} := \frac{\ell_{plane}}{2} \qquad T_{plane} := W_{plane} \cdot cg_{plane} \qquad T_{plane} = 62.836 \, \mu N \cdot \mu m$$

THERMAL ACTUATOR $$x_{ta} := 15 \, \mu m \qquad F_{ta} := \left( 64.644 \cdot \frac{\mu N}{\mu m} \right) x_{ta} \qquad F_{ta} = 969.66 \, \mu N$$

FIG. 2C

INFORMATION FOR α FOUND AT
http://www.ae.msstate.edu/~masoud/Teaching/pics/A6.4_table_A6.1.gif $$\alpha := \frac{\left(\frac{w_{axis}}{t_{axis}} - 2.0\right)}{2.5 - 2.0} \cdot (0.258 - 0.246) + 0.246 \qquad \alpha = 0.257$$

$$\tau_{max} := \frac{T_{tot}}{\alpha \cdot w_{axis} \cdot t_{axis}^2} \qquad \tau_{max} = 3.817 \times 10^7 \, Pa$$

$$\theta_{axis} := \frac{T_{tot}}{G_{poly} \cdot I_p} \qquad \theta_{axis} = 2.426 \, \frac{1}{m}$$

$$\gamma_{max} := \frac{\tau_{max}}{G_{poly}} \qquad \gamma_{max} = 4.944 \times 10^{-5}$$

$$\varepsilon_{max} := \frac{\gamma_{max}}{2} \qquad \varepsilon_{max} = 2.472 \times 10^{-5}$$

$$\sigma_{max} := E_{poly} \cdot \varepsilon_{max} \qquad \sigma_{max} = 3.955 \times 10^6 \, Pa$$

$$\sigma_{max} < U_{poly} = 1$$

FIG. 2E

Y-DIRECTIONAL FORCE PER TURNSTYLE AND PER ACTUATOR

$$F_{per} := \frac{F_{pin\_y}}{2}$$

REQUIRED FORCE PER ACTUATOR FOR 6 TURNSTYLES AND 2 ACTUATORS

$$F_{required} := \frac{F_{per}}{12} \qquad \boxed{F_{required} = 0.181 \ \mu N}$$

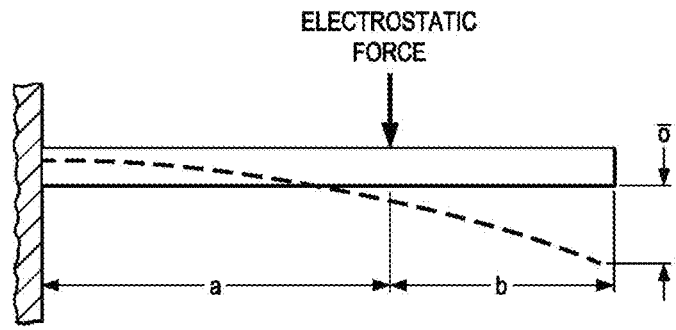

SNAP DOWN FORCE REQUIRED

$$\delta = \left(\frac{P \cdot a^3}{6EI}\right) \cdot (3L - a)$$

$L := 500 \ \mu m$  $\qquad x := 250 \ \mu m$ $a := L - x$  $\qquad \delta := 2 \ \mu m$ $h := 1 \ \mu m$  $\qquad E := 0.16 \ \dfrac{N}{\mu m^2}$ $b := 20 \ \mu m$ $$P := \frac{6 \cdot \delta \cdot E \cdot b \cdot h^3}{12 a^2 \cdot (3L - a)} \qquad \boxed{P = 0.041 \ \mu N}$$

FIG. 2F

GRABBING FORCE

$\text{FORCE}_{provided} := 970 \ \mu N$ $\text{FORCE}_{grabbing} = \text{FORCE}_{provided} \cdot \cos(\theta_{arm})$

ELECTROSTATIC SNAP-DOWN

$\varepsilon_0 := 8.85 \cdot 10^{-12} \ \frac{F}{m}$ $\qquad A_0 := 320 \ \mu m \cdot 60 \ \mu m$ $d_0 := 6.8 \cdot 10^{-6} \ m$ $\qquad E_{poly} = 1.6 \times 10^{11} \ Pa$ $t_0 := 2.25 \cdot 10^{-6} \ m$ $\qquad L_0 := 320 \cdot 10^{-6} \ m$ $V_0 := \frac{2 \cdot d_0}{3} \cdot \sqrt{\frac{4 \cdot E_{poly} \cdot t_0^3 \cdot d_0}{9 \cdot L_0^4 \cdot \varepsilon_0}}$ $\qquad V_0 = 34.926 \ V$ $F_0 := \frac{\varepsilon_0 \cdot A_0 \cdot V_0^2}{2 \cdot d_0^2}$ $\qquad F_0 = 2.241 \times 10^{-6} \ N$

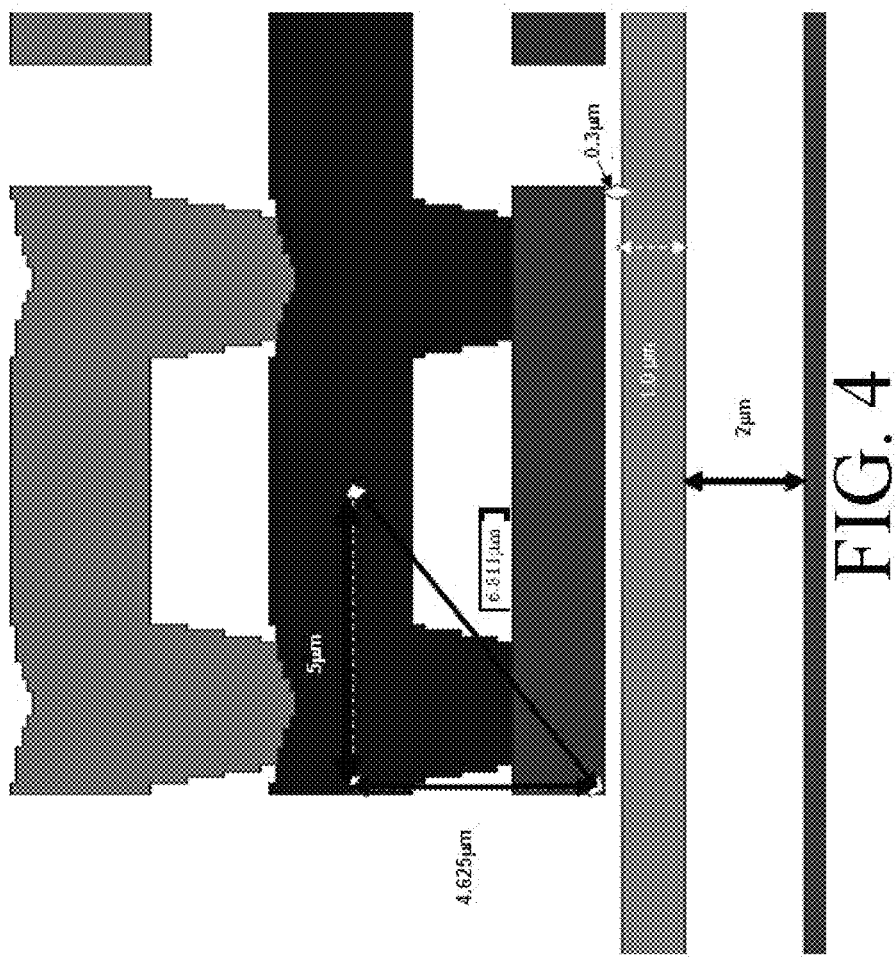

| Bond Pad | Application |
|---|---|
| 1A* | When 4-6 V are run through these bond pads, this will displace the thermal actuator and activate the jacking system, disengaging the latch holding down the operating plane. |
| 1B | Same as 1A. |
| 2A | When 4-6 V are passed through these bond pads, the displacement of thermal actuator will activate the jacking system, drawing a set of crossbars past a pin which is attached perpendicular to the axle of the operating plane. This will put a torque on the axle and thus cause the entire operating plane to rotate upward. |
| 2B | Same as 2A |
| 2C | These bond pads will require approximately 35 V, and it will pull down the hot and ground leads. The leads need to be pulled down to allow the operating plane the freedom to rotate. Once the plane is fully rotated, current to these bond pads will be removed, which will allow the leads to regain contact with the base of the operating plane. This will allow power to reach the top of the plane. |
| 3 | These will require 4-6 V, and they will supply power to the tool at the top of the operating plane. This voltage should only be applied when operating plane is orthogonal to the horizontal Plane. The procedure for when voltage should be applied depends on the tool that is attached to the top of plane. With the tool that is currently attached to the top of the plane, a voltage needs to be applied to Bond Pad 3 in order for the arm to extend and grab. |

* "Refers to Hot VIA and Ground GNDIA. This nomenclature is consistent for all other bond pads as well.

FIGURE 5

| Organism | Shape | Measured Breaking Pressure | Radius | Wall Thickness | Measured Breaking Pressure |
|---|---|---|---|---|---|
| | | atm | μm | μm | Mpa |
| S. typhimurium | Cylindrical | 100 | 0.25 | 0.003 | 10.13 |
| C. eugametos | Spherical | 95 | 8 | 0.060 | 9.63 |
| B. emersonii | Spherical | 65 | 10 | 0.45 | 6.59 |
| D. caroia | Spherical | 30 | 30 | 0.1 | 3.04 |
| | | | | | |

FIG. 7C

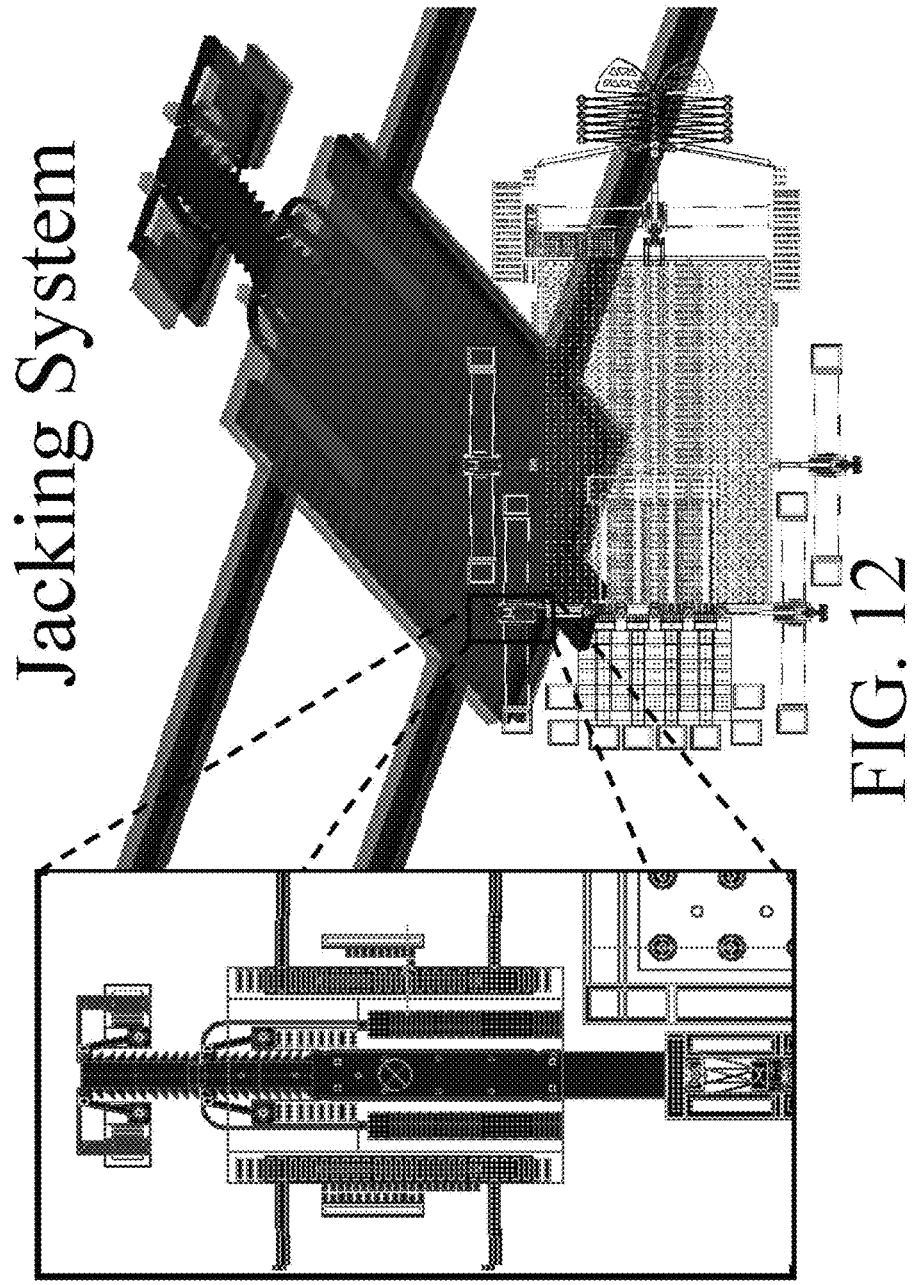

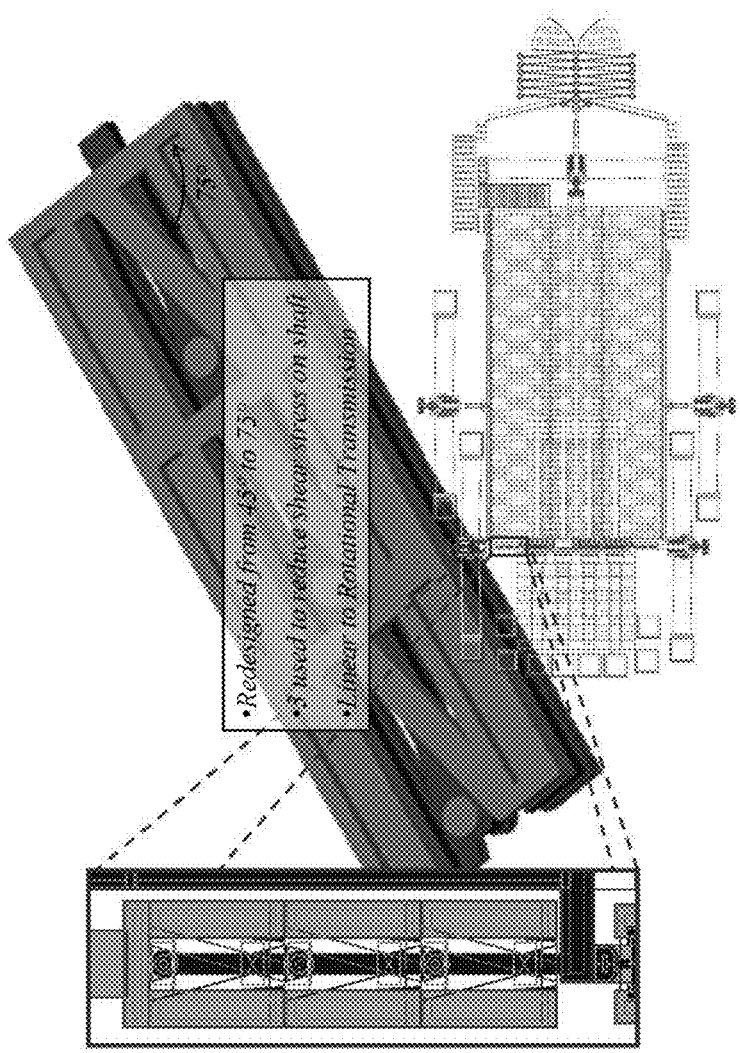

Geometric Concerns
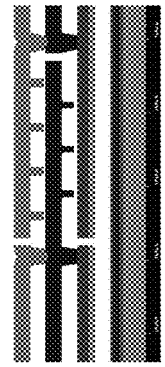
The pin that holds the plate down during the release wash. This must be pulled back before the plate can be raised.
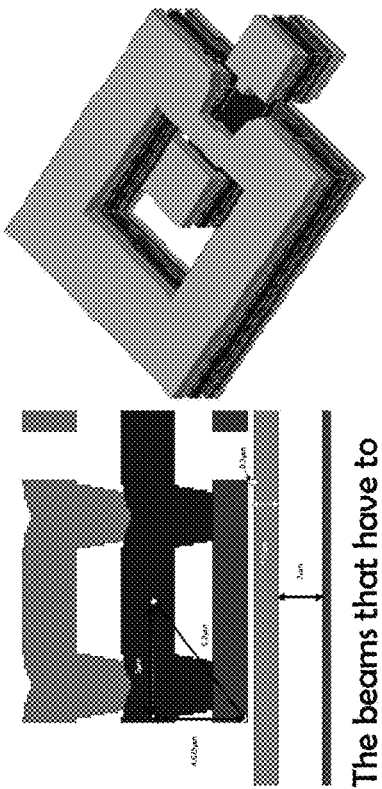
The guide for the plate as it rises. There are five of these to help lock the plate into a vertical and horizontal position.
The beams that have to clear the rotation of the plate.
FIG. 16

Tool Set

- Pliers
- Cutting tool
- Extension Device
- Hot Knife
- Magnetic Bead Implanter Gun
- Biopsy Tool Application For Shark Jaws
Carbon Nanotube Manipulation

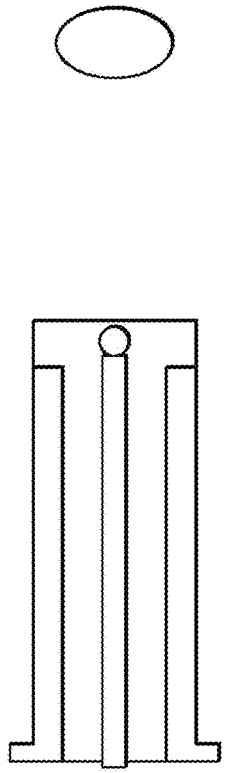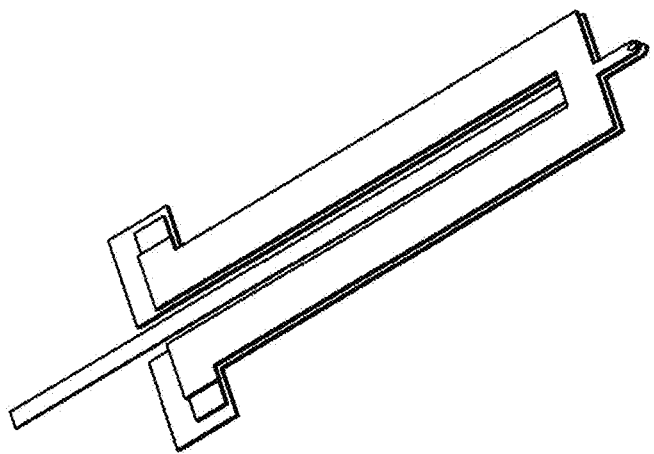
FIG. 21

Cauterizing Tool
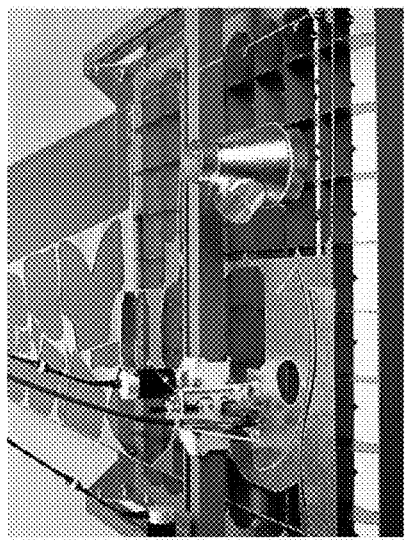
Thermal actuator arms can be used as a tool
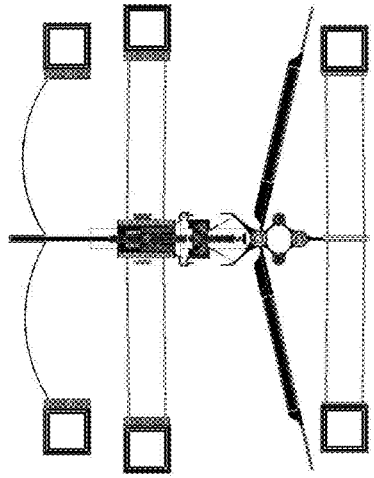
- Joule heats to 500K and higher
- Has a reach upwards of 50 μm
- Can retract to allow multiple pass cuts and various depths
FIG. 24

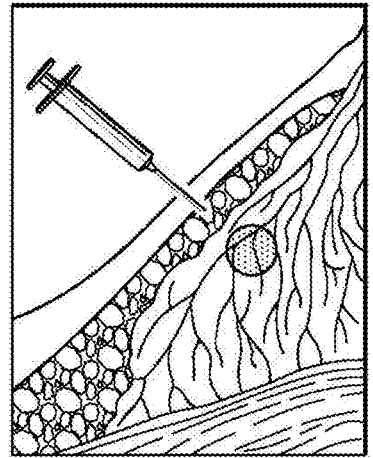
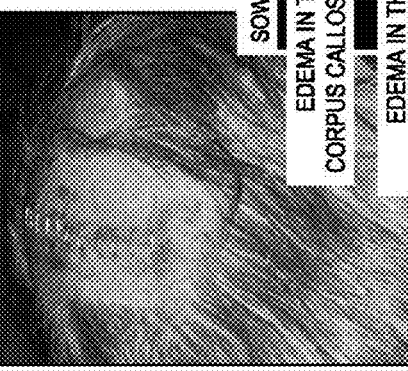
FIG. 25

Grounded Case, Encased Hot Lead

Side Bumpers Secure OP in Release

THREE DIMENSIONAL (3D) ROBOTIC MICRO ELECTRO MECHANICAL SYSTEMS (MEMS) ARM AND SYSTEM

CLAIM OF PRIORITY

This application claims priority under 35 USC § 120 to U.S. patent application Ser. No. 14/247,021, filed on Apr. 7, 2014, which will issue as U.S. Pat. No. 9,473,048 on Oct. 18, 2016; which claims priority under 35 USC § 120 to Ser. No. 13/406,454, filed on Feb. 27, 2012, and now issued as U.S. Pat. No. 8,689,899 issued on Apr. 8, 2014; which claims priority under 35 USC § 120 to U.S. patent application Ser. No. 12/470,474, filed on May 21, 2009, and now issued as U.S. Pat. No. 8,122,973 issued on Feb. 28, 2012; which claims priority under 35 USC § 119(e) to U.S. Provisional Patent Application Ser. No. 61/055,038, filed on May 21, 2008, the entire contents of all and which are hereby incorporated by reference.

TECHNICAL FIELD

This invention relates to Micro Electro Mechanical Systems (MEMS), and more particularly to a three dimensional (3D) MEMS arm and system.

BACKGROUND

Micro ElectroMechanical Systems (MEMS) integrate mechanical elements, sensors, actuators, and/or electronics on a common silicon substrate through micro fabrication technology. The electronics are often fabricated using integrated circuit (IC) process sequences. The micromechanical components are often fabricated using compatible micromachining processes that selectively etch away parts of the silicon wafer or add new structural layers to form the mechanical and electromechanical devices.

MEMS devices generally range in size from a micrometer (a millionth of a meter) to a millimeter (thousandth of a meter). Common applications include: inkjet printers that use piezoelectrics or bubble ejection to deposit ink on paper, accelerometers in cars for airbag deployment in collisions, gyroscopes in cars to detect yaw and deploy a roll over bar or trigger dynamic stability control, pressure sensors for car tire pressure, disposable blood pressure sensors, displays based on digital light processing (DLP) technology that has on a chip surface several hundred thousand micro mirrors and optical switching technology for data communications.

SUMMARY

A micro assembly have a substrate and an operating plane coupled to the substrate. The operating arm is movable from an in-plane position to an out-of-plane position. One or more electric connections provide electric power from the substrate to the operating plane in the out-of-plane position. A tool is coupled to the operating plane. The tool is operable to receive electric power from the operating plane to perform work.

The tool may be, for example, pliers, cutting tool, extension device, hot knife, magnetic bead implanter gun, and biopsy tool. Thus, the micro assembly may perform specific functions in three dimensions, such as reaching above and beyond the plane of the chip in order to do work or to obtain and retrieve tangible objects for analysis.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-F illustrate force information for the MEMS device;

FIG. 4 illustrates one embodiment of rotation geometry;

FIG. 5 illustrates further details of the bond pads in accordance with one embodiment;

FIGS. 7A-C illustrate one embodiment of a magnetic bead implanter gun and cell breaking points;

FIGS. 12-49 illustrate further details of the MEMS device, including various tools and applications, and fabrication of the device.

DETAILED DESCRIPTION

Figure 1:
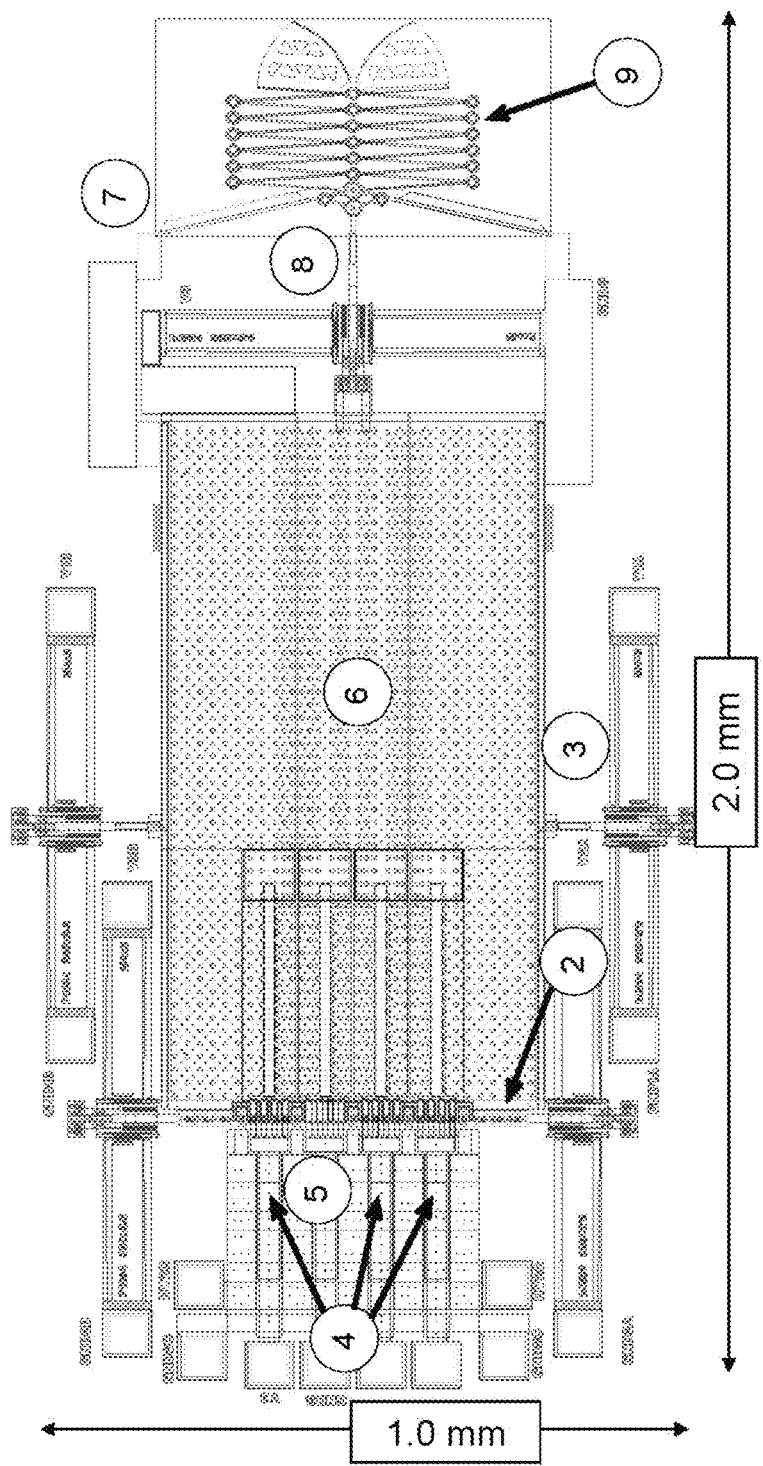
FIG. 1 illustrates one embodiment of a MEMS device in accordance with the present disclosure.

FIG. 1 illustrates one embodiment of 3D MEMS device that operates at significant elevation levels (greater than 1 mm) and performs activities. The device contains an arm that raises into a position orthogonal to the chip, allowing one of several different tools to come into contact with the space above the chip. Potential tools operated by the device could include one of any number of different mechanical devices: measuring tools, tools suitable for medical applications such as biopsies, etc.

The device has three major components. First, using on-chip actuation, this design automatically rotates a structure with sizable length (e.g., mm) to a vertical position that is orthogonal to the plane of the chip. Second, the device is designed to provide electrical power (insulated hot and ground leads) to the top of the vertical structure once it is upright. Third, at the top of the vertical structure which rises significantly above the substrate, it provides real estate space for micro-tools that move and perform work. The micro-tool has a telescopic accordion-like arm with the ability to reach up and grab something over 300 µm above the top of the elevated structure which is about 1.5 mm above the substrate of the chip. In summary, the device is the realization of several features including, for example, automatic 90 degrees rotation of released MEMS structures into vertical orientations, electrical power supplied up through the elevated structure, and micro-tool work and movement at the top of the elevated structure. Applications include nanotechnology, biomedical, micro-manufacturing, micro-fluidics, and micro-sensors. Applications include reaching up above chip to perform tasks, reaching out off chip to perform tasks and providing power and/or power leads out of plane. Other applications include medical applications including: micro-surgery, cut or grab a micro-hunk of tissue, microsurgical tool, monitoring of bodily functions from inside the body on the micro scale, collecting data or samples on the micro scale, fertilized egg turner. Micro-tooling applications include micro-sensing, measuring micro distances, using MEMS robot to construct other micro-structures, and using MEMS robot to repair objects on the micro scale grabber, extension arm, micro cutter and micro activator.

The device contains an arm that raises into a position orthogonal to the chip, allowing one of several different tools to come into contact with the space above the chip. Electrical contacts may extend between the out-of-plane platforms and the in-plane platform. The different tools allow the device to become one of any number of different mechanical devices: a measuring tool, a cutter, a grabber, a manipulator, or a specialized tool designed to complete a specific task.

The geometry of MEMS devices creates a product that is, in effect, a two and half dimensional object. Therefore, having the ability to raise part of the device and interact in the third dimension will give MEMS devices new and progressive 3-D abilities. There are numerous potential applications, including interaction with a second chip in a flip-chip or other system or allowing the raised chip to interact on a new level within its working environment. While structure can be raised up manually (e.g., probe tip actuation), the device, using on-chip actuation, will erect itself into a vertical orientation using its own means. In addition, electrical power will run up the vertical structure in order to run the micro-tools at the end of the operating plane. The 3-D micro-robot may perform micro-tasks in the 1 mm to 2 mm range distances above the surface of the chip. The 3-D micro-robot may perform micro-tasks in the 1 mm to 2 mm range distances off the edge of the chip. The 3-D micro-robot may perform micro-tasks using electrical energy in the 3 to 50 volts range with current less than 1.0 milliamp. Designs may fit within the standard 2820μ×6340μ module chip size.

Referring to FIG. 1, the device includes ground lead 1, provides a ground for the tools on the top of the operating plane. Hot lead 2 includes three hot leads. One hot lead is provided for every thermal actuator required to do a function (i.e. extend the arm, close the grabber, etc.). These leads connect into the encased oxide (garage) portions of the operating plane. Thermal actuators with jacking system 3 uses teeth to incrementally move the jacking system forward. Pin and cross system 4 uses a set of angled cross bars that when drawn forward, apply a force on a set of pins orthogonally attached to the axle of the operating place. This results in a torque on the axle which causes the operating plane to rate 90°. There are three cross members on each side of the rotating axle with 15° between the two cross members. Thermal actuators and latches 5 keep the operating plane secure while it is not being elevated. Operating plane 6 is the main body that is being elevated. The circles are the pores in the operating place. They allow etching trough to the substrate layer which will release the operating plane 6 from the surface of the chip. In operating plane 6 contains a series of structures of encased oxide (garages) that will allow P3 to be insulated and serve as the hot lead for the tool 9. Tool connection 7 connects to the tool 9 to provide rigidity, and this is also where the thermal actuator connects for its ground. Thermal actuator for tool 8 may be a smaller thermal actuator than the others, so it can fit on the top of the operating plane. It contains a jacking system to allow the tool to reach its full extension. Tool 9 may be the scissor action extension arm or other tool option.

In regard to the thermally actuated jack lift system 3, the operating plane 6 is to be raised 90 degrees by the thermally actuated jacking system 3. The jack itself is simply a thermal actuator with a ratcheting centerpiece designed to incrementally drive a series of cross member components. Each actuation motion travels about 10 μm, and the ratchet teeth are each separated by 4 μm. This means that each actuation pushes the cross members two teeth, or 8 μm.

Figure 2B:
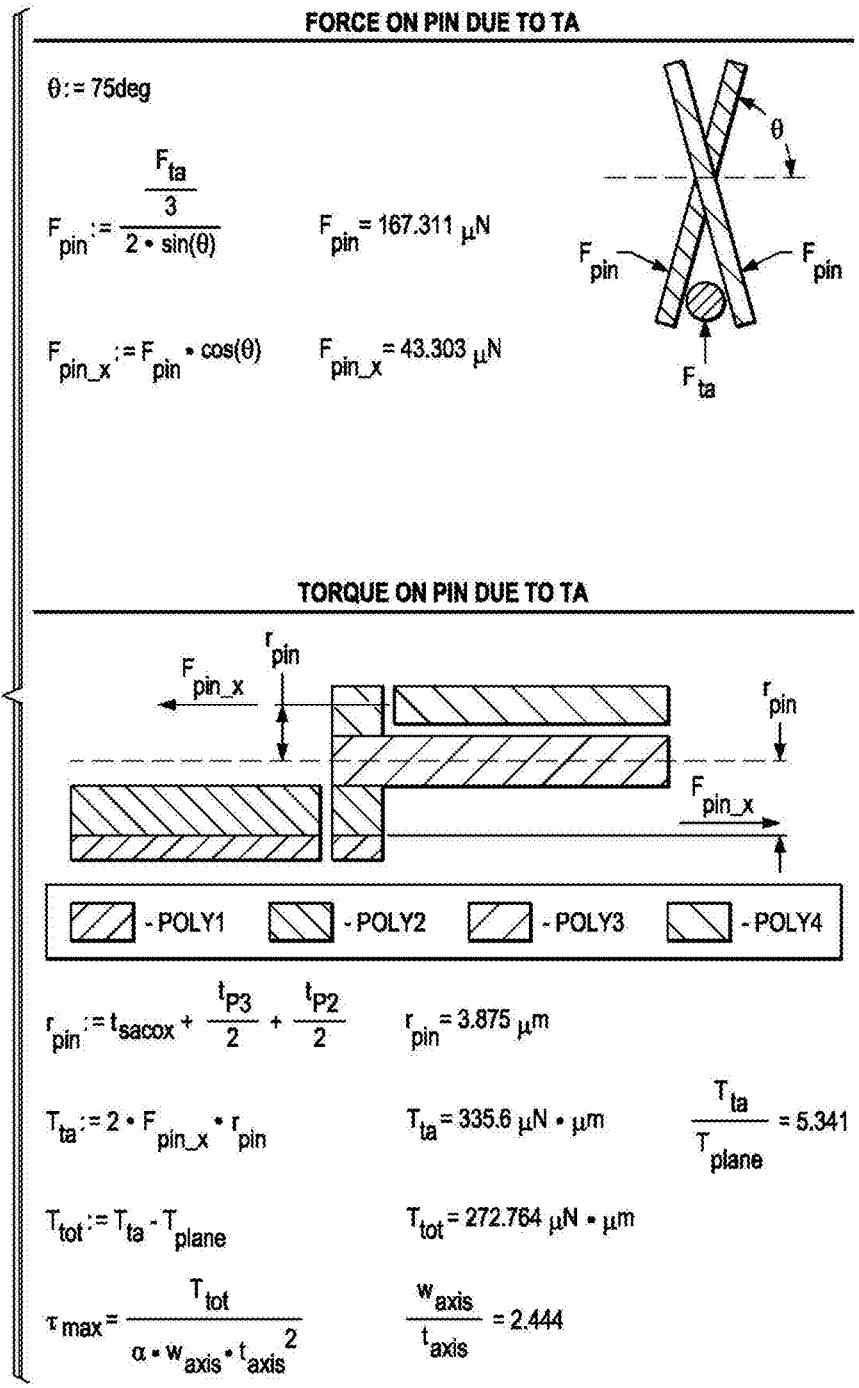
Figure 2D:
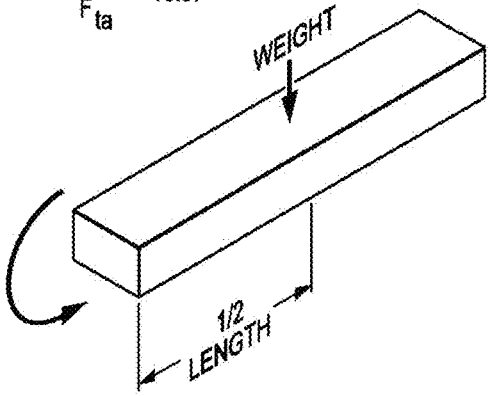

The cross member components are designed to translate the force provided by the thermal actuators in order to put a torque on the operating plane pivot axle. Pins that are fixed perpendicularly to the axle are guided by the cross members along a path that is 15 degrees off of the axis. This allows the torque to incrementally raise the operating plane 6 to a position orthogonal to the MEMS chip. The total distance that the cross member components need to travel is 18 μm. This means that 2.25 actuations are required to reach 90 degrees. There are a total of 6 cross member components; a larger number of cross members reduces the force required for the thermal actuators to achieve plane rotation. Mathematical proofs of FIG. 2 illustrate the key force information for the MEMS system.

In regard to the operating plane latch system 5, during the release phase of the SUMMiT V fabrication process, there are turbulent forces that can potentially damage a design if the device is not properly secured to the chip. To minimize the potential for damage, a set of thermally actuated latches will he utilized to safeguard the device. Located on either side of the operating plane (i.e. the plane to be raised), the latches will secure the plane to the chip face until it is time to raise the plane. At such time, the latches will be released by activating the thermal actuators, which in turn will free the operating plane from the face of the chip.

Figure 3:
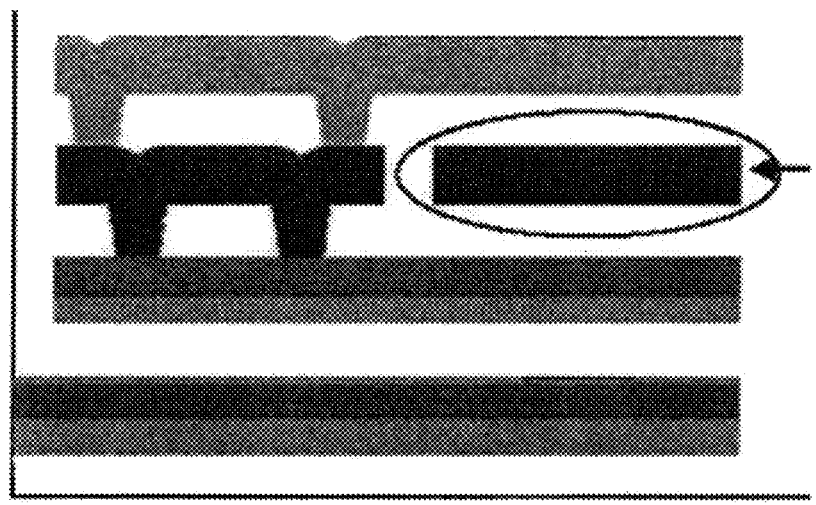
FIG. 3 illustrates one embodiment of an electrical wire in the MEMS device.

In regard to the operating plane 6, the operating plane provides stability, electrical current, and be the proper size to give height off the face of the chip. To do this a 1.4795×0.8 mm plane designed that is electrically charged and fastened at its base to a torsional lift axle. The plane may have the capacity for up to 6 separate circuits, though the main design requires only 2. The interior of the operating plane 6 is perforated by release pores, to ensure separation of the 3 structural polysilicon layers from the substrate material of the chip. Also on the interior are the 'hot' sides of the electrical tool circuits. To do this, polysilicon layer 3 is encapsulated in segmented shafts that run the length of the plane. The shafts are long shells constructed using polysilicon layers 1, 2, 3, and 4 (also referred to as P1, poly1, etc.). Layers 1 and 2 serve as the bottom faces of the shell, layer 4 serves as the top face, and layer 3 serves as the side rails. A single strand of polysilicon layer 3 is separated from the shell by the encased oxide and will run the length of the shaft. In effect, electrical 'wires' have been created that enable current to be carried to the tool mounted at the top of the operating plane. See FIG. 3. Along the side edges of the operating plane 6 run segments that act as grounds for the electrical circuits.

In regard to leads 1 and 2, the purpose of the leads is to bring power to the plate when it is raised to 90 degrees. To accomplish this, 3 hot leads and three ground leads are provided that, when the plate is in place, will connect to the leads which run through the core of the plate. Before the plate can be raised these leads need to be pulled out of the way to clear the path of motion. The geometry for this rotation is illustrated in FIG. 4. Electrostatic forces are used to accomplish this. By running a lead along the base plate that is next to, but not directly beneath, the main leads, a conductor can be used on top of each beam to pull it down without letting it touch the conductor. This prevents a short circuit that would cause the beam to release back to its original position. During the raising of the plate both the ground and hot leads will be bent out of the way to allow the plate to pass. Once the plate passes, the leads will be released and allowed to contact the bottom of the elevated plan thus completing the circuit. This is will provide power to the top of the plate. To ensure this component will work properly it is necessary to calculate the force developed by the charge field below the beam, so that the proper voltage is passed through the conducting plate. These calculations allow the actual tip displacement of the beam to be estimated using beam theory. From the calculation for one beam, the force needed to lower the beam a distance of 2 μm is 2.241 μN. To generate this force it is necessary to have a charge difference of approximately 35 volts between the plates. This voltage must be somewhat higher in practice due to the number of arms to be lowered and because it is not an ideal situation. After examining the geometry of the plate bottom and its rotation, the minimum amount the leads can be lowered to allow for clearance is 1.89 μm. In order to allow for the plate to shift it is advisable to lower it as far as possible, which will be 2 μm.

One major area of concern in the original design of the lifting mechanism for the plate was running power up to the top. In fact this was one of our main design objectives. One of the challenges facing the design team was to be able to raise the plate and then connect the power in such a way that the power lines did not interfere with the plate on its way up. To accomplish this the leads were designed as cantilever beams that could be stressed out of the way and allowed to snap back in to position after the plate was raised to its full height. For this application the team chose to use an electrostatic pull down effect on the beams to bend them low enough to gain the clearance required. Using the formulas for beam bending and electromagnetic attraction force between parallel plates, the team was able to derive a method to not only determine the voltage required to "snap down" our current design, but how a redesign could be done to reduce the voltage required and to prevent arcing between the charged plate and the beam being pulled.

Part of the design takes into account the possibility of a short circuit; this involved placing the actual beam having the electrostatic force applied in the layer above the beam that needed to be cleared of the plate. Thus, the team assured that the beam would not touch any layers. This change in design had major effects on the math model for the electrostatic snap down, because the force that was being applied over an area was being transferred to a non-central non-end point on a different beam. This required the use of the parallel plate force equation and the non-central point beam deflection equation, each using the size and shape of the respective beam. Basic assumption could be made: the beam would act linearly in bending, the cross section would remain uniform, and the electromagnetic field produced by the base charging plate would be uniform. For simplicity sake the force on the beam due to gravitational acceleration was ignored as well. With these assumptions in place the entire equation became a simple algebraic expression with either data values that the design team could set or change as needed, or material constants. From this simple equation the team was able to derive an expression for the voltage required to move the beam a certain maximum distance. Once the maximum distance that the beam can moved has been obtained, work can go into determining the actual distance it would have to travel to clear the rotation of the operating plane. Then those beams could snap back in to place and link up for the required In regards to the scissor action extension gripper or other tool 9, the scissor action extension gripper is located at the end of the operating plane and provides the ability to extend a tool beyond the plane surface. Two gripping jaws, named shark jaws, are attached to the end of the extension system, allowing the device to grasp three-dimensional objects as the system extends. There are a multitude of micro tools 9 that can be affixed to the gripper system (wrenches, sensors, cutters, etc.).

The scissor action extension gripper is powered by a single thermal actuator, which is connected to a bearing on the jack system 3. As the thermal actuator is charged and displacement occurs, the bearing is pulled by the thermal actuator. The bearing is connected to a stationary bearing on the jacking system 3 through a series of bearings and beams. The stationary bearing has two functions as the pivot point for the jacking system 3 and as the connection for the struts that hold the jack system 3 in place. To the right of the stationary bearing lies the device that performs the action of extension. It is essentially 3 rows of 5 bearings per row, each connected by a simple beam. As the thermal actuator pulls on the bearing, the angles of the beams decrease, thus causing the beams to extend in the opposite direction of the thermal actuator's pull. The decreasing angle of the beams thus causes the shark jaws to clasp towards each other.

The shark jaws have serrated edges in order to minimize the surface contact between the jaws and the object to be grasped. As the contact area between the two surfaces is decreased, the magnitude of Van der Waal's and stictional forces is decreased, facilitating the release of the object.

The extension distance of the gripper is a function of the thermal actuator's displacement. A maximum thermal actuator displacement of 15 μm results in a reach distance of 319.41 um. There is a linear relationship between the displacement of the thermal actuator and how far the gripper reaches into space. The relationship can be expressed as:

$$\text{Extension} = (\delta_{TA}) * 21.214$$

Where: $\delta_{TA}$=Displacement of the thermal actuator

The force exerted by the teeth of the shark jaws is dependent on two parameters the displacement of the thermal actuator and the location of the contact paint between the jaws and the object to be grasped. An object near the end of the shark jaws' grasp will most receive as much force as an object near the joint or pivot point of the jaws. This force is dependent on the moment at the pivot point for the jaws.

$$M = \left(\frac{F_{TA}}{2}\right)\delta_V$$

Where: $\delta_V$=Vertical displacement of the bearing attached to the thermal actuator
$F_{TA}$=Force exerted by the thermal actuator which is 612.5 μN The linear relationship between the displacement of the thermal actuator ($\delta_{TA}$) and $\delta_V$ can be expressed as $\delta_V = -(1.196.36\delta_{TA} = 59.611$ (see appendix C). Using this relationship, the force exerted at the contact point on the jaws can be expressed as:

$$F(x_0, \delta_{TA}) = \frac{M}{x_0} = \frac{F_{TA}\delta_V}{2x_0} = \frac{F_{TA}((-0.1963)(\delta_{TA}) + 59.611)}{2x_0}$$

Where: $x_0$=Distance from the joint of the jaws to the contact point

Regarding the bond pads, FIG. 5 provides details of the bond pads and their applications.

The device, in the SUMMiTV application, relies on being able to use the interaction of the cross-members in P1, P2, and P4 with the bar in P3 to create rotational movement. Additionally the gripper system uses P1, P2, and P4 to make two separate bars beams to extend in the opposite direction of the thermal actuator's pull. The decreasing with hinge pins that are comprised of P1, P2, P3 and P4, allowing the bars to rotate and the scissor-jack to expand and contract.

The Sandia Ultra-planar, Multi-level MEMS Technology 5 (SUMMiT V™) Fabrication Process is a five-layer polycrystalline silicon surface micromachining process (one ground plane/electrical interconnect layer and four mechanical layers). It is a batch fabrication process using conventional IC processing tools. Using this technology, high volume, low-cost production can be achieved. The processing challenges, including topography and film stress, are overcome using methods similar to those used in the SUMMiT V™ Process: topography issues are mitigated by using Chemical-Mechanical Polishing (CMP) to achieve planarization, and stress is maintain at low levels using a propriety process.

MEMS are also produced in the SUMMiT V™ Fabrication Process by alternately depositing a film, photolithographically patterning the film, and then performing chemical etching. By repeating this process with layers of silicon dioxide and polycrystalline silicon, extremely complex, inter-connected three-dimensional shapes can be formed. The photolithographic patterning is achieved with a series of two-dimensional "masks" that define the patterns to be etched. The SUMMiT V™ process uses 14 individual masks in the process.

The functionality of the micro-robotic arm lies in its ability to accommodate a wide assortment of tools for a variety of purposes. The tools 9 are detailed below.

Figure 6A:
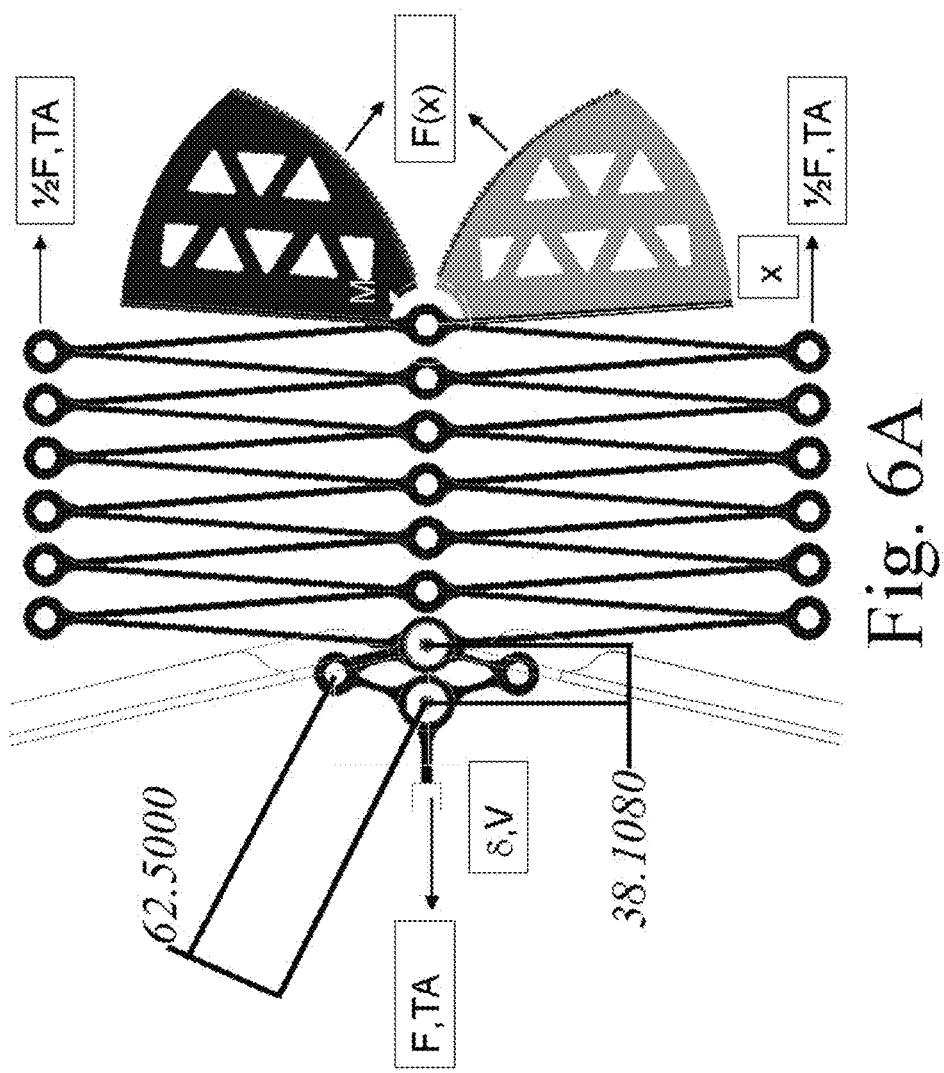
FIGS. 6A-C illustrate one embodiment of the shark-jaws.

FIG. 6A illustrates the scissor action extension gripper 20. It is located at the end of the operating plane and provides the ability to extend a tool beyond the plane surface. Two gripping jaws, named shark jaws, are attached to the end of the extension system, allowing the device to grasp three-dimensional objects as the system extends. There are a multitude of micro tools that can be affixed to the gripper system (wrenches, sensors, cutters, etc.).

The scissor action extension gripper is powered by a single thermal actuator, which is connected to a bearing on the jack system. As the thermal actuator is charged and displacement occurs, the bearing is pulled by the thermal actuator. The bearing is connected to a stationary bearing on the jacking system through a series of bearings and beams. The stationary bearing has two functions as the pivot point for the jacking system and as the connection for the struts that hold the jack system in place. To the right of the stationary bearing lies the device that performs the action of extension. It is essentially 3 rows of 5 bearings per row, each connected by a simple beam. As the thermal actuator pulls on the bearing, the angles of the beams decrease, thus causing the beams to extend in the opposite direction of the thermal actuator's pull. The decreasing angle of the beams thus causes the shark jaws to clasp towards each other.

The shark jaws have serrated edges in order to minimize the surface contact between the jaws and the object to be grasped. As the contact area between the two surfaces is decreased, the magnitude of Van der Waal's and stictional forces is decreased, facilitating the release of the object.

Figure 6B:
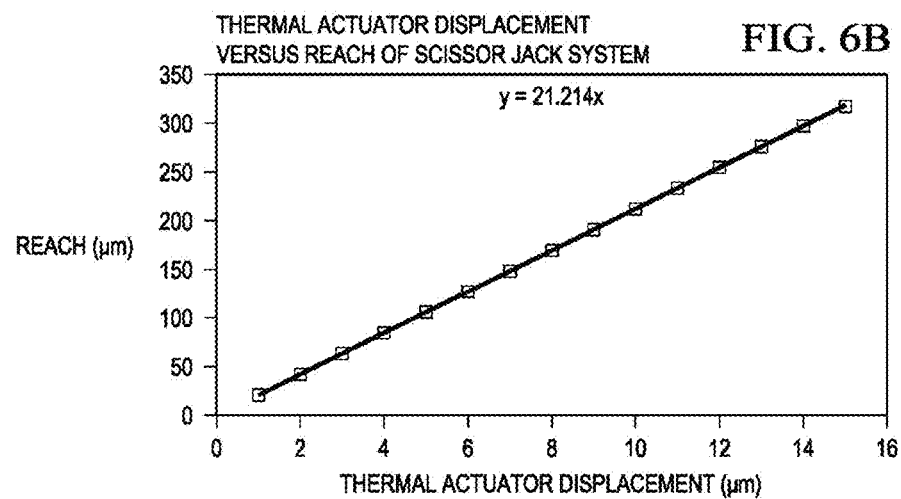
Figure 6C:
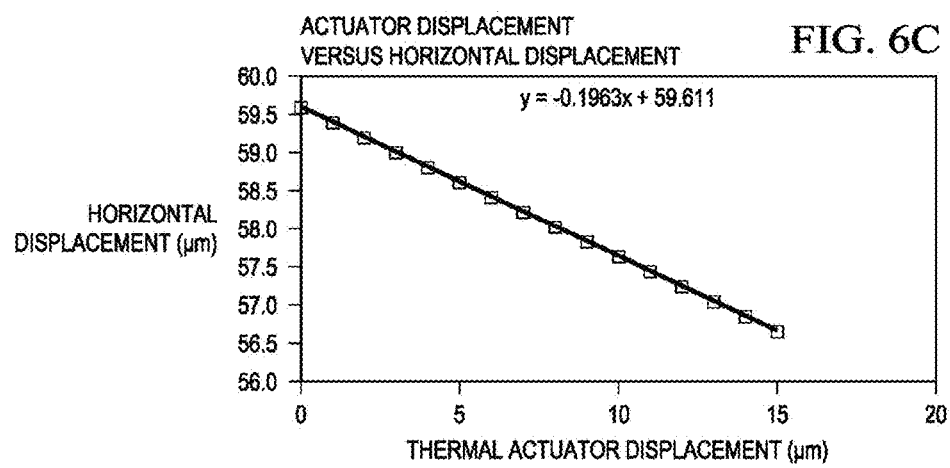

The extension distance of the gripper is a function of the thermal actuator's displacement. A maximum thermal actuator displacement of 15 μm results in a reach distance of 319.41 μm. There is a linear relationship between the displacement of the thermal actuator and how far the gripper reaches into space (see FIG. 6B). The relationship can be expressed as:

$$\text{Extension} = (\delta_{TA})*21.214$$

Where $\delta_{TA}$-Displacement of the thermal actuator

The force exerted by the teeth of the shark jaws is dependent on two parameters: the displacement of the thermal actuator, and the location of the contact point between the jaws and the object to be grasped. An object near the end of the shark jaws' grasp will not receive as much force as an object near the joint, or pivot point, of the jaws. This force is dependent on the moment at the pivot point for the jaws.

$$M = \left(\frac{F_{TA}}{2}\right)\delta_V$$

Where: $\delta_V$—Vertical displacement of the bearing attached to the thermal actuator
$F_{TA}$—Force exerted by the thermal actuator, which is 612.5 μN The linear relationship between the displacement of the thermal actuator ($\delta_{TA}$ and $\delta_V$ can be expressed as: $\delta_V = -0.1963\delta_{TA}+59.611$ (see FIG. 3). Using this relationship, the force exerted at the contact point on the jaws can be expressed as:

$$F(x_0, \delta_{TA}) = \frac{M}{x_0} = \frac{F_{TA}\delta_V}{2x_0} = \frac{F_{TA}((-0.1963)(\delta_{TA}) + 59.611)}{2x_0}$$

Where: $x_0$—Distance from the joint of the jaws to the contact point.

Figure 7A:
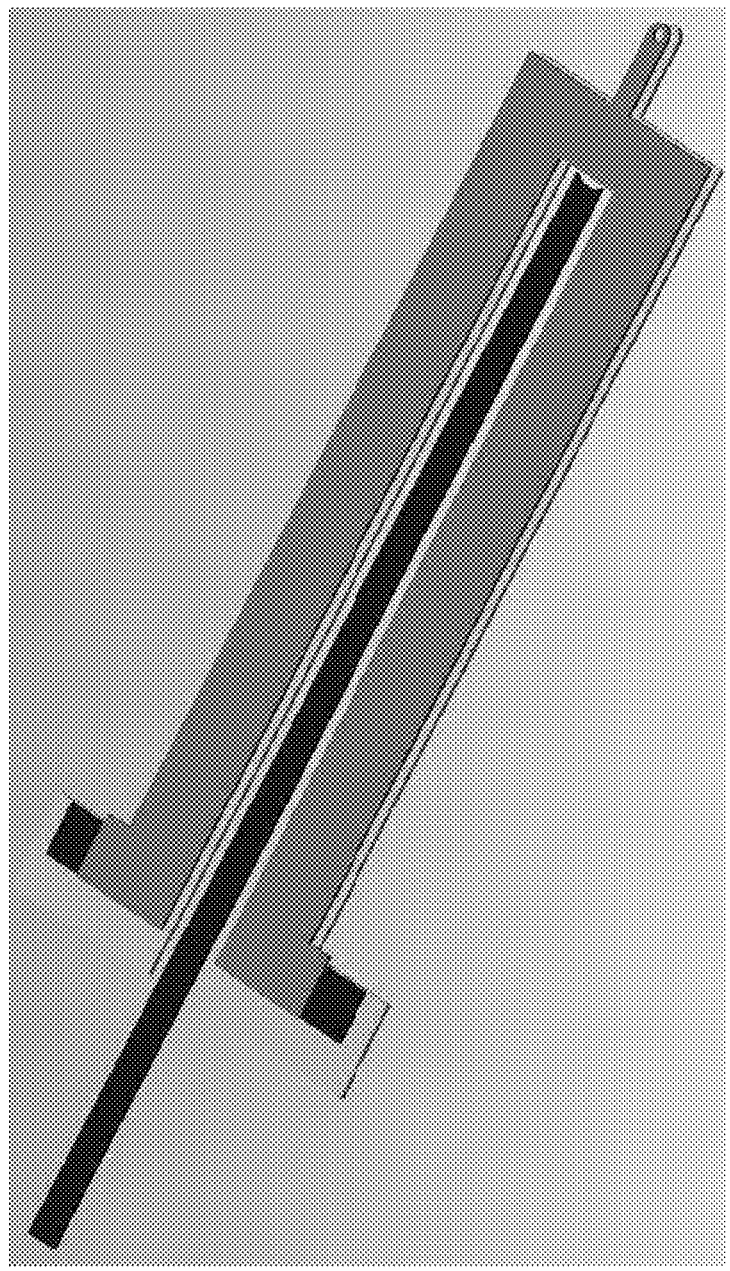
Figure 7B:
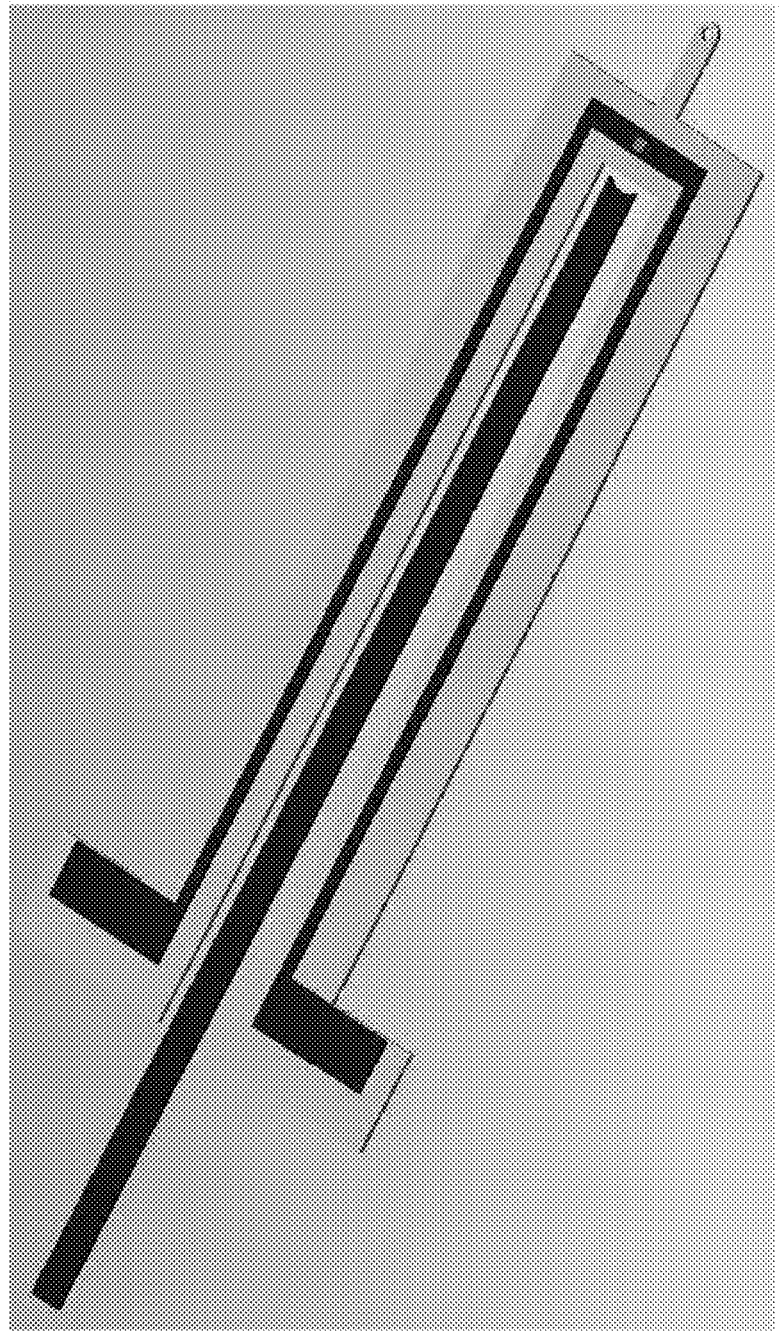

FIGS. 7A and 7B illustrates a magnetic bead implanter gun 30. The problem with current magnetic bead technologies is the failure to specifically target an individual cell for sorting purposed. In order to affix magnetic beads to a certain type of cell, the beads are put into solution with the cells and then randomly attract to one another. This can be problematic If the researcher only wants to collect a unique cell out of a group. The magnetic bead implanter gun (MBIG) solves this problem by shooting a single bead into an individual cell, breaking the membrane and becoming Immersed m the cell's cytoplasmic fluid.

The magnetic bead is fit into the two circular holes at the end of the MBIG. The holes serve the purpose of holding the magnetic bead in place because the magnetic bead's diameter is much greater than the holes' diameter.

Cold finger technology is used in the MBIG to secure the magnetic bead while the operating plane rotates into an orthogonal position. The P2 and P4 layers actually hold onto the magnetic bead while the P3 layer provides the thermal expansion necessary for the MBIG's deformation. The P3 layer is attached to the P4 layer via a small square of Sac-Ox near the end of the gun, and as a current is applied to the P3 layer it expands and consequentially raises the P4 layer a distance of several microns. Once expanded, a magnetic bead can be placed between the layers.

The bead is shot from the MBIG via a ramming rod that is connected to a thermal actuator. When the thermal actuator is activated and physically displaced, this drives the ramming rod into the bead. The ramming rod is in P3, so it is necessary for the P3 layer attached to the body of the gun to thermally expand and rise out of the way so the layers will not collide upon impact.

The MBIG is designed so that a bead can successfully puncture a cell's exterior membrane. FIG. 7C shows several varieties of single celled organisms and their corresponding pressures needed to break the cell membrane. The salmonella cell has the largest measured breaking pressure with 10.13 MPa, so the MBIG should deliver a bead at a relatively higher pressure. The pressure exerted on the bead can be calculated by dividing the thermal actuator's exerted force by the area of the ramming rod that impacts the bead, or:

$$P = \frac{F}{A} = \frac{612.5 \; \mu N}{14 \; \mu m \times 2.25 \; \mu m} = 19.44 \; MPa$$

Thus, the MBIG delivers an appropriate pressure to break the membrane of a cell. It should also be noted that the cell will not be permanently damaged by this process. Due to the elastic properties of cells, they will actually expand in order to accommodate the newly acquired magnetic bead. Once the magnetic bead is inside the cell, it will be manipulated with an electromagnetic field in order to maneuver the cell-bead pair to a desired location.

Figure 8:
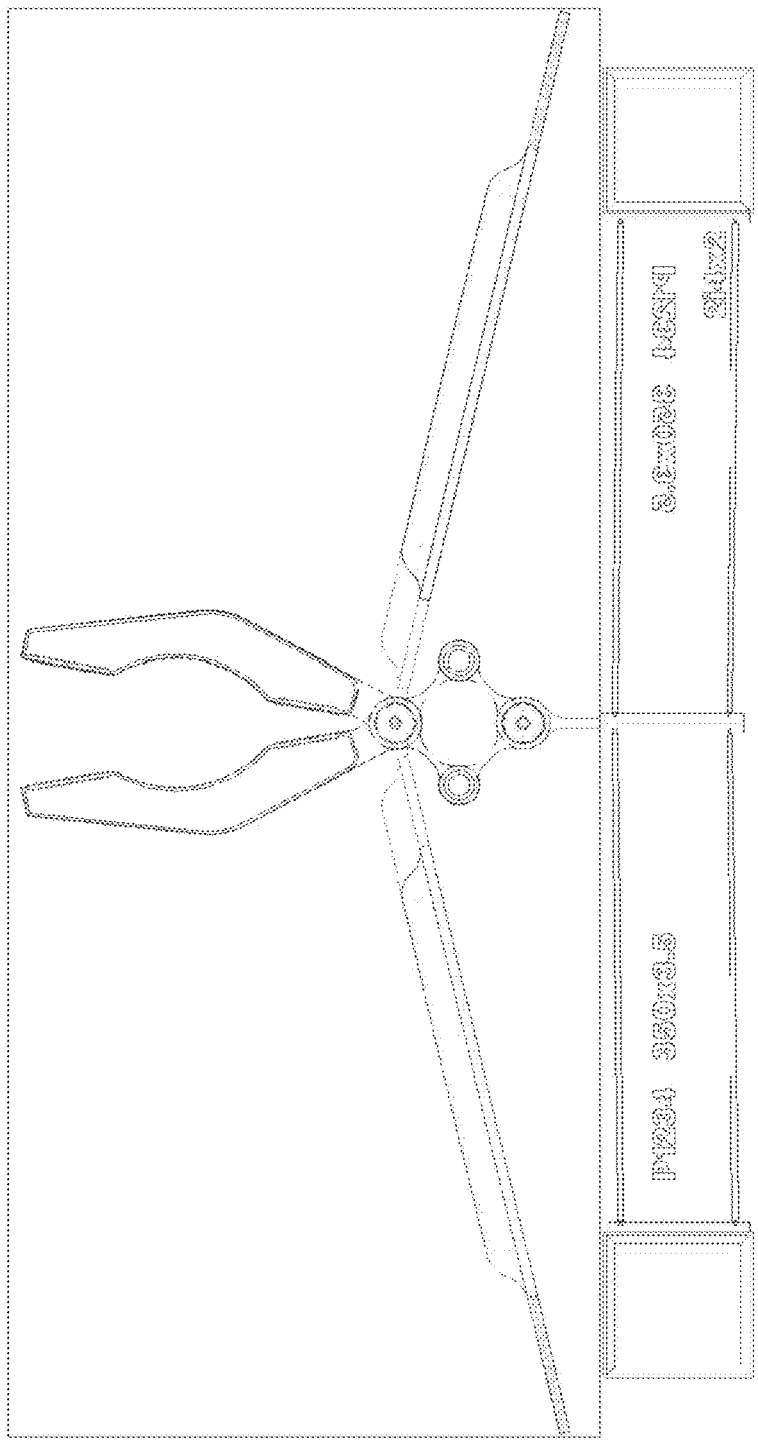
FIG. 8 illustrates one embodiment of micropliers.

FIG. 8 illustrates micropliers 40. Due to an enlarged contact surface area, the micropliers are an ideal tool for holding onto large objects. The pliers are driven by a thermal actuator that pulls on a bearing that is connected to a stationary bearing through a series of beams. The stationary bearing serves as the pivot point for the pliers and as the connection for the struts.

Figure 9:
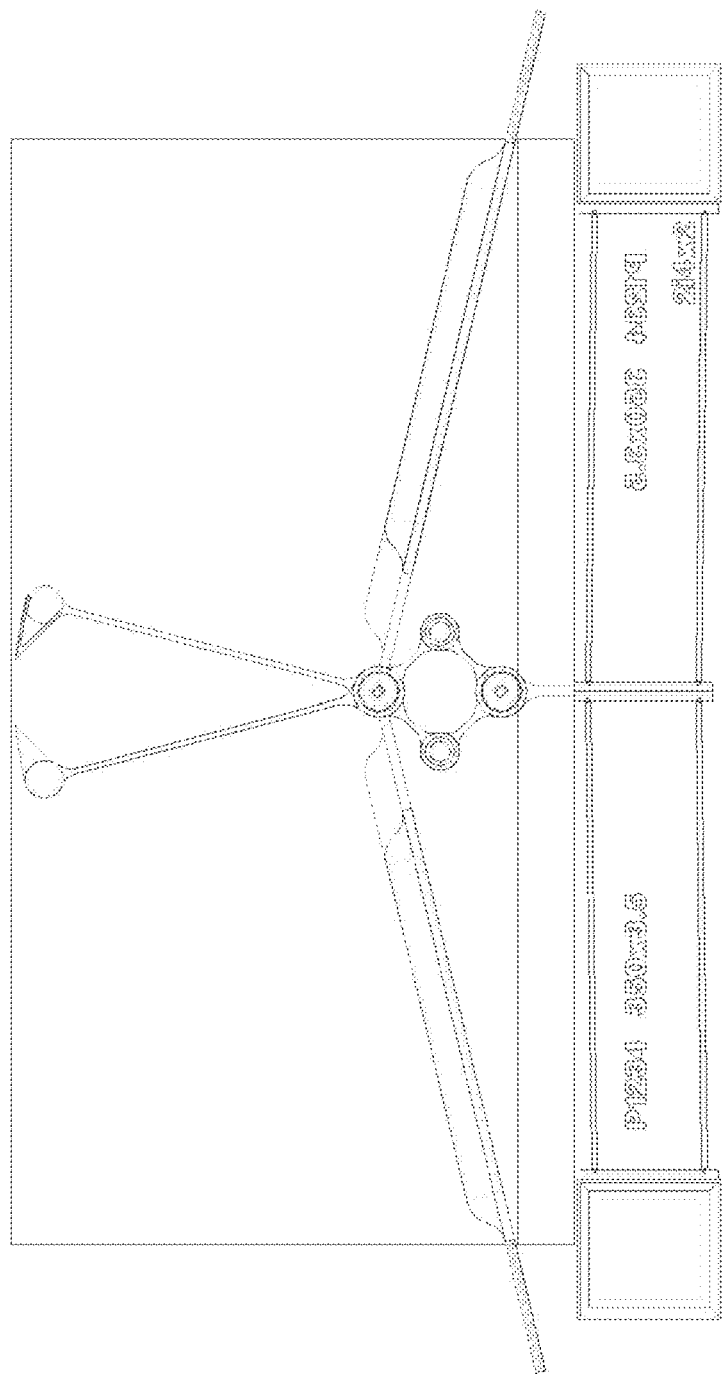
FIG. 9 illustrates one embodiment of a cutting tool.

FIG. 9 illustrates cutting tool 50. The cutting tool was designed to cut an object with its sharp edges. Driven by the same mechanism as the micropliers, the two heads of the tool pull together and pinch a very small contact area. The elongated beams of the cutting tool allow for a greater moment to occur at the pivot point, resulting in a higher force exerted at the contact point.

Figure 10:
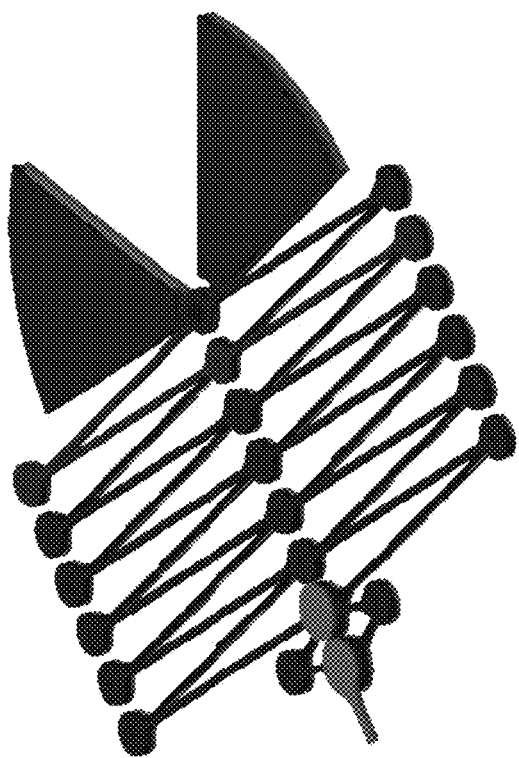
FIG. 10 illustrates one embodiment of a biopsy tool.
Figure 11A:
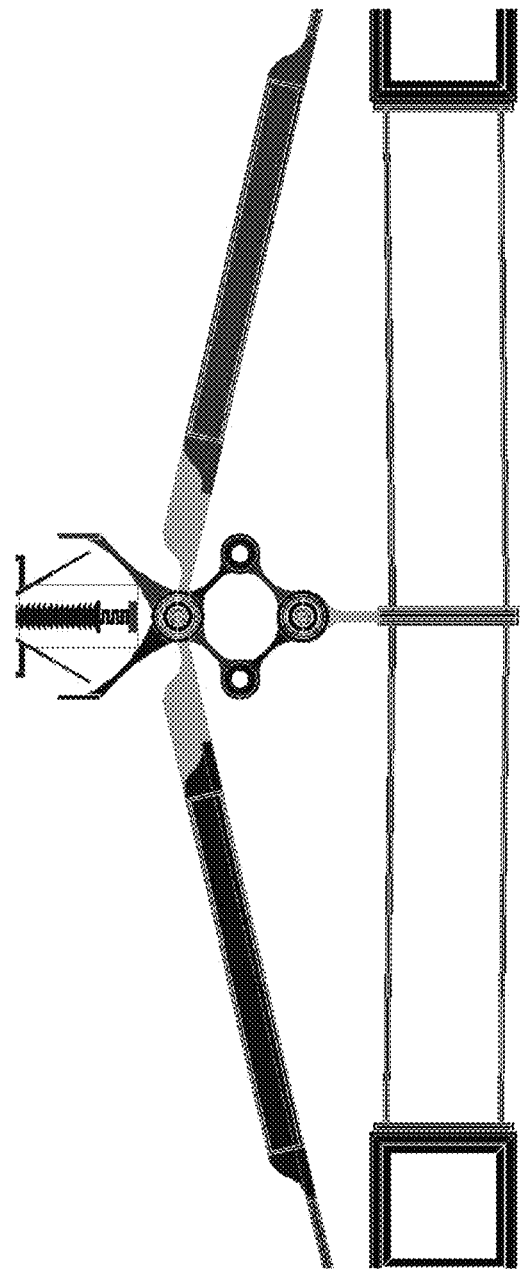
FIGS. 11A-D illustrates a cauterizing tool.
Figure 11B:
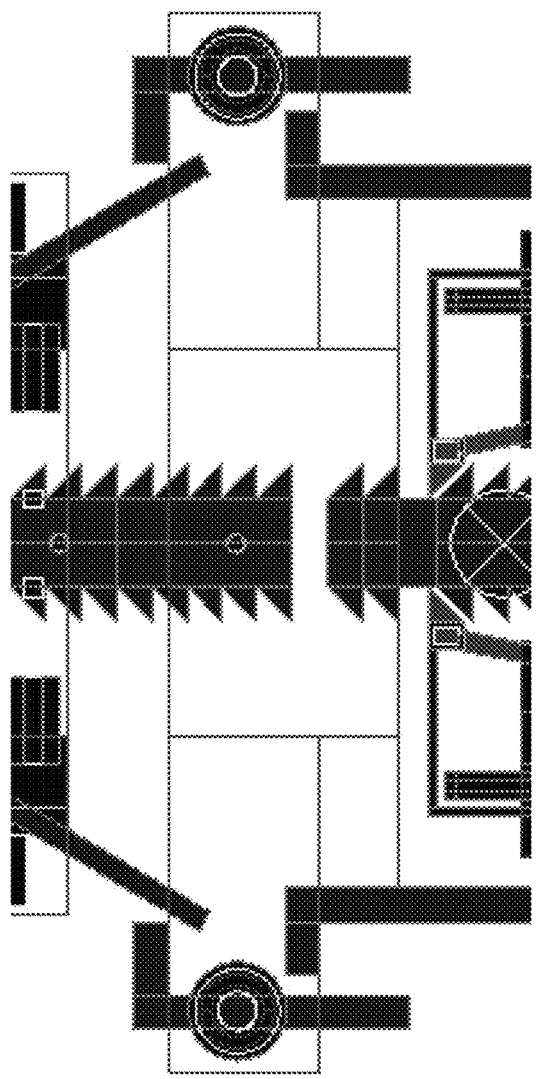
Figure 11C:
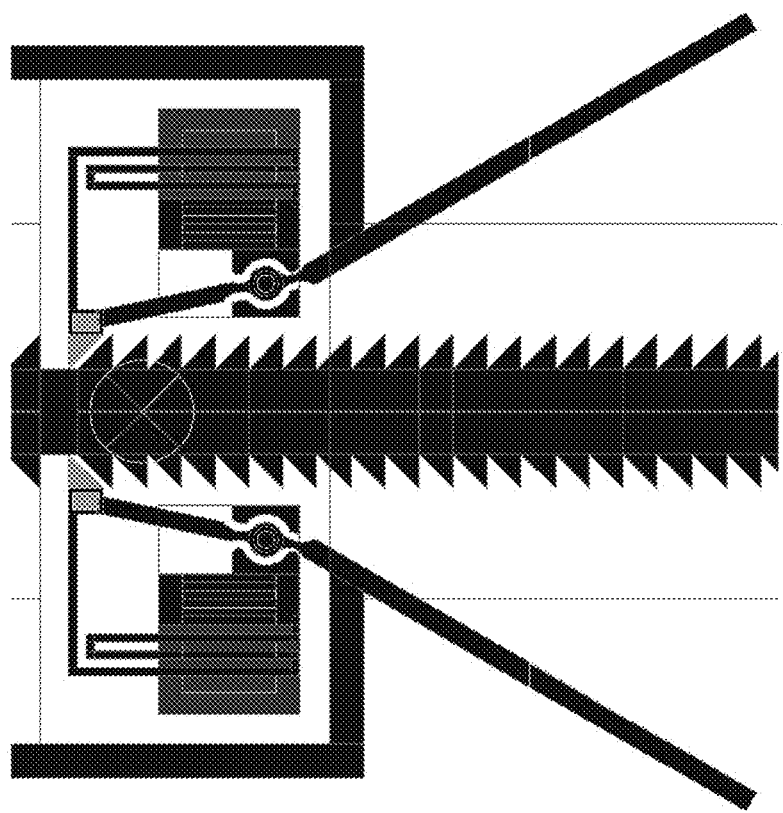
Figure 11D:
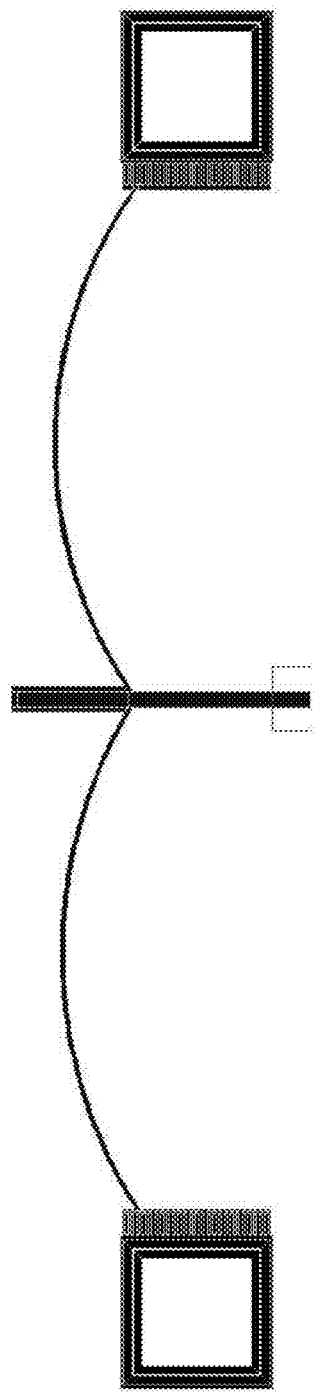
Figure 14:
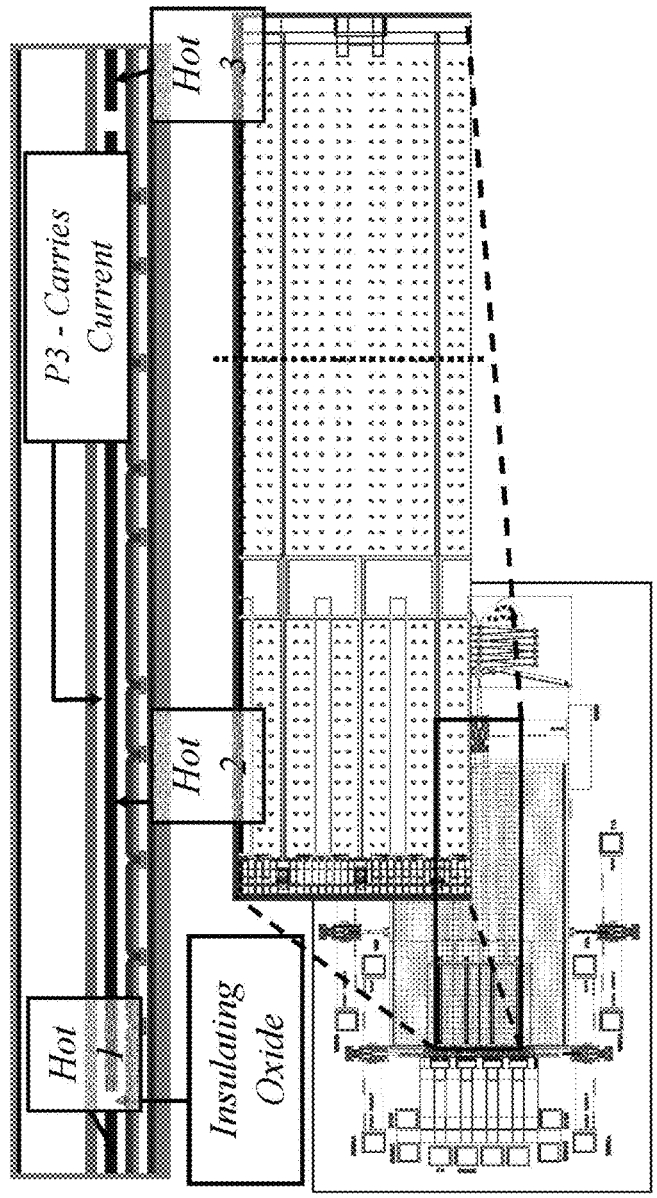
Figure 15:
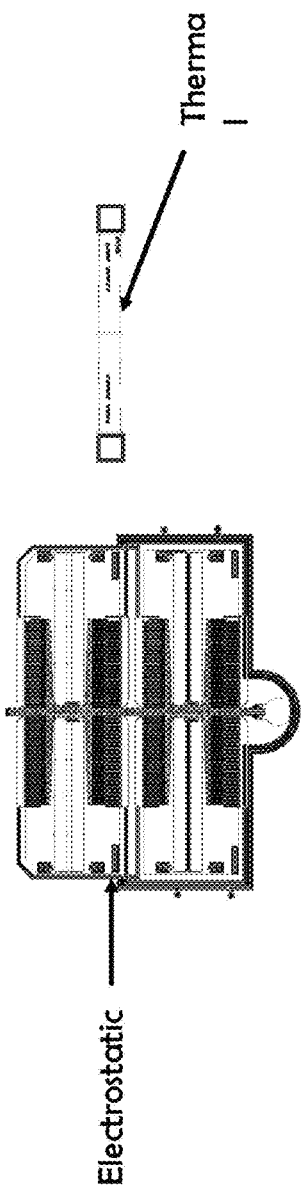
Figure 17:
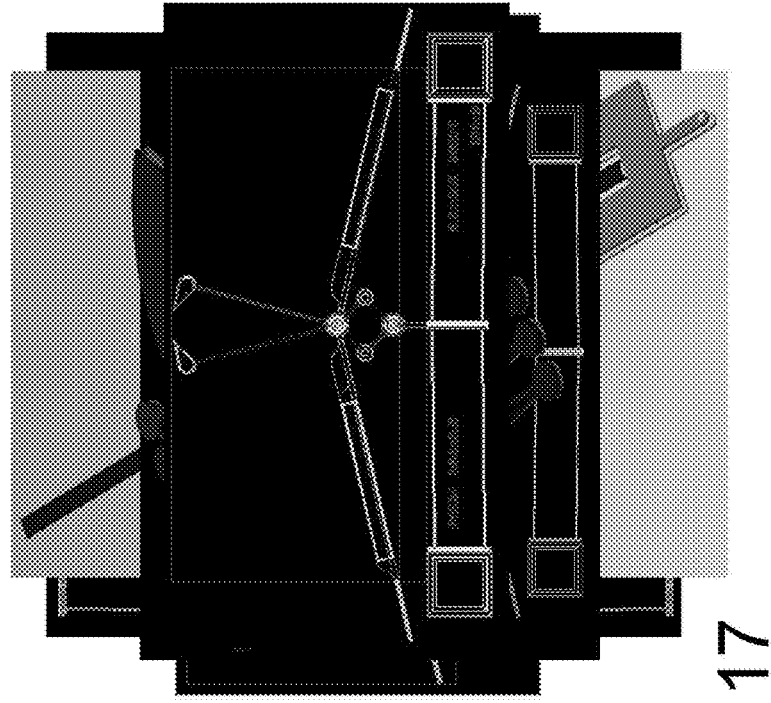
Figure 18:
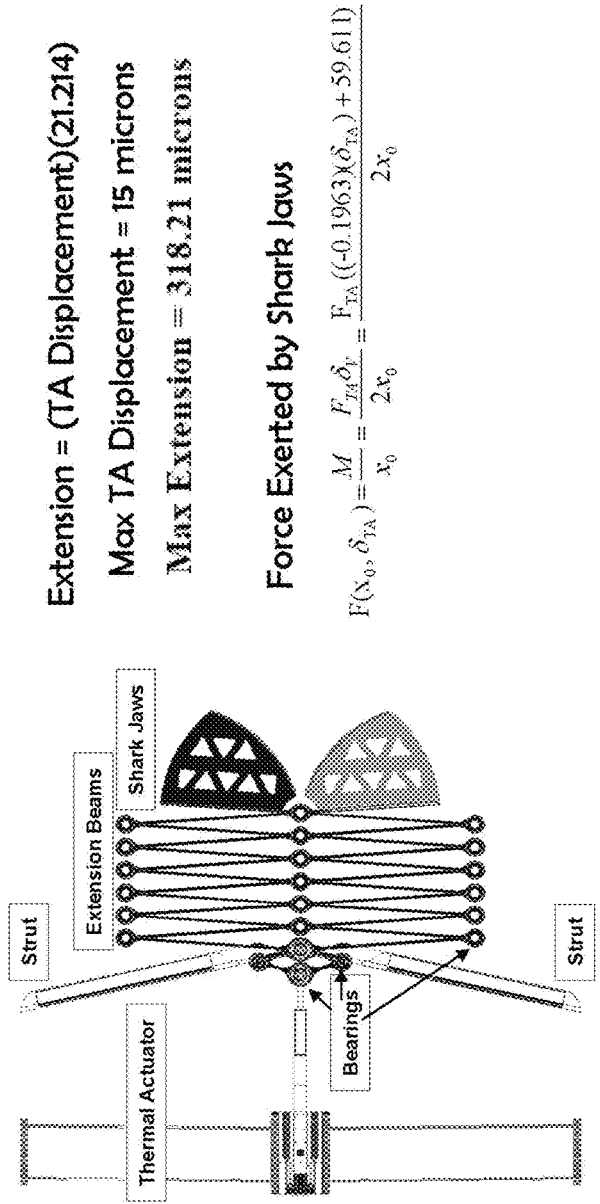
Figure 19:
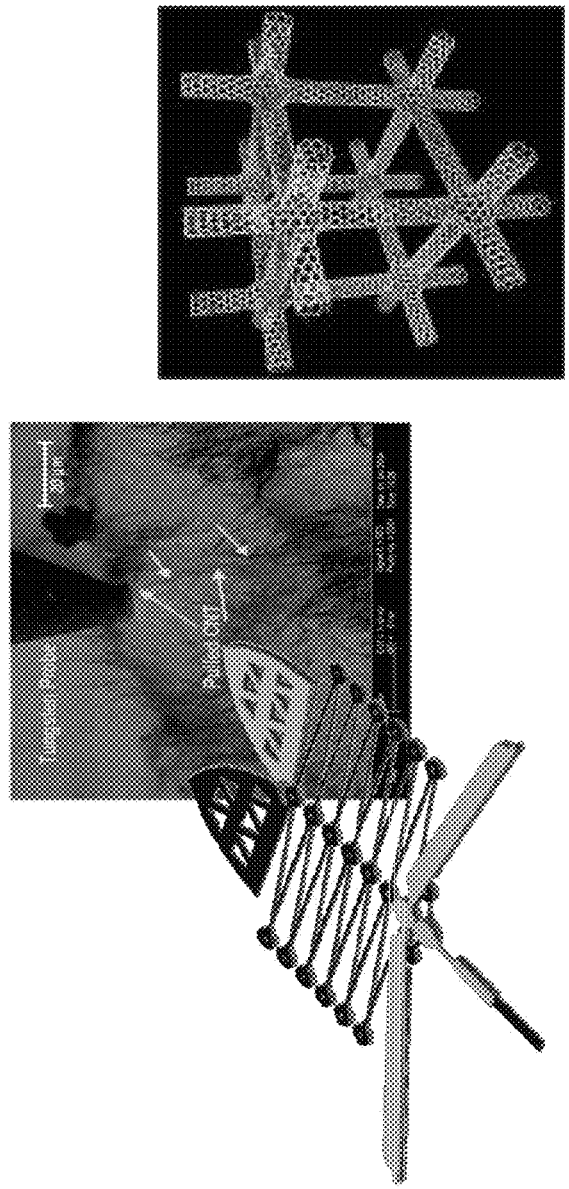
Figure 20:
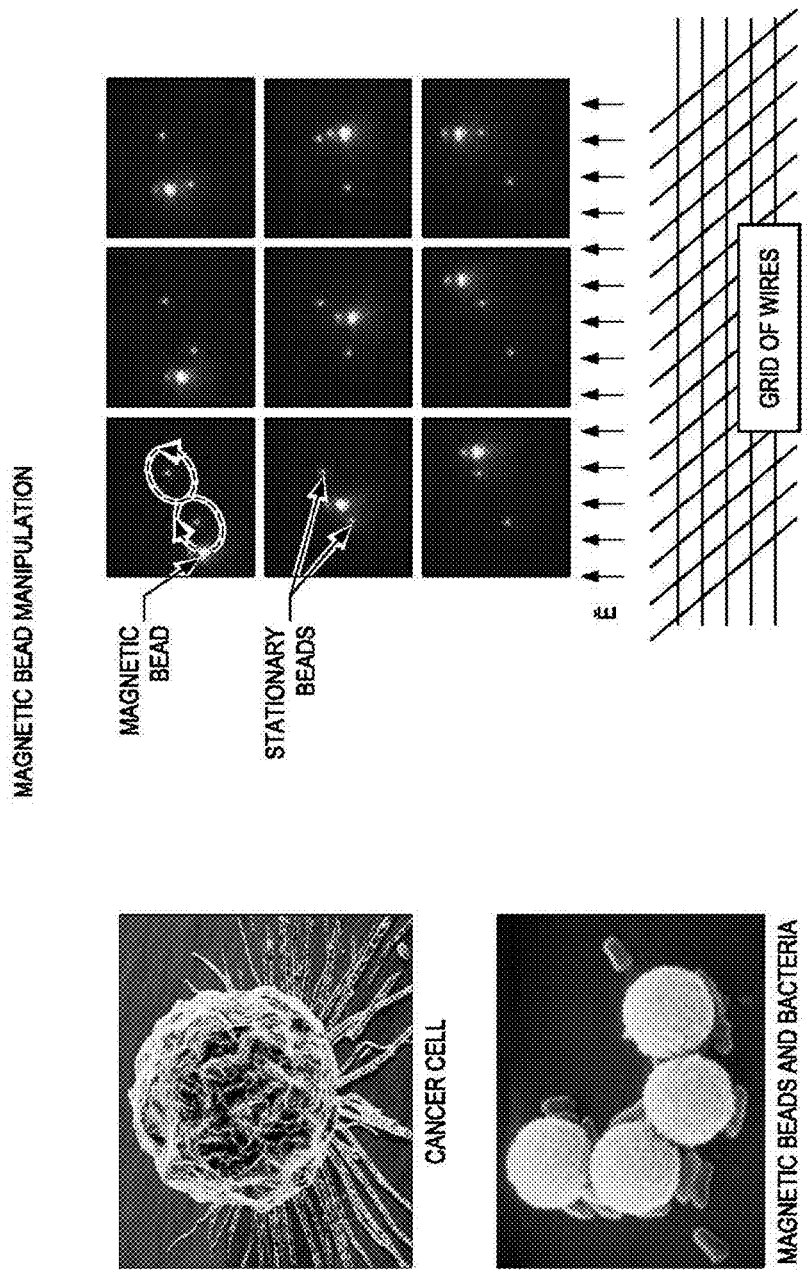
Figure 22:
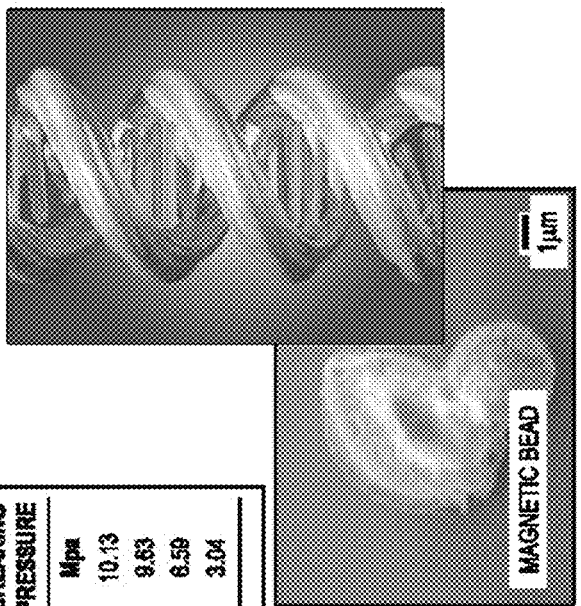
Figure 23:
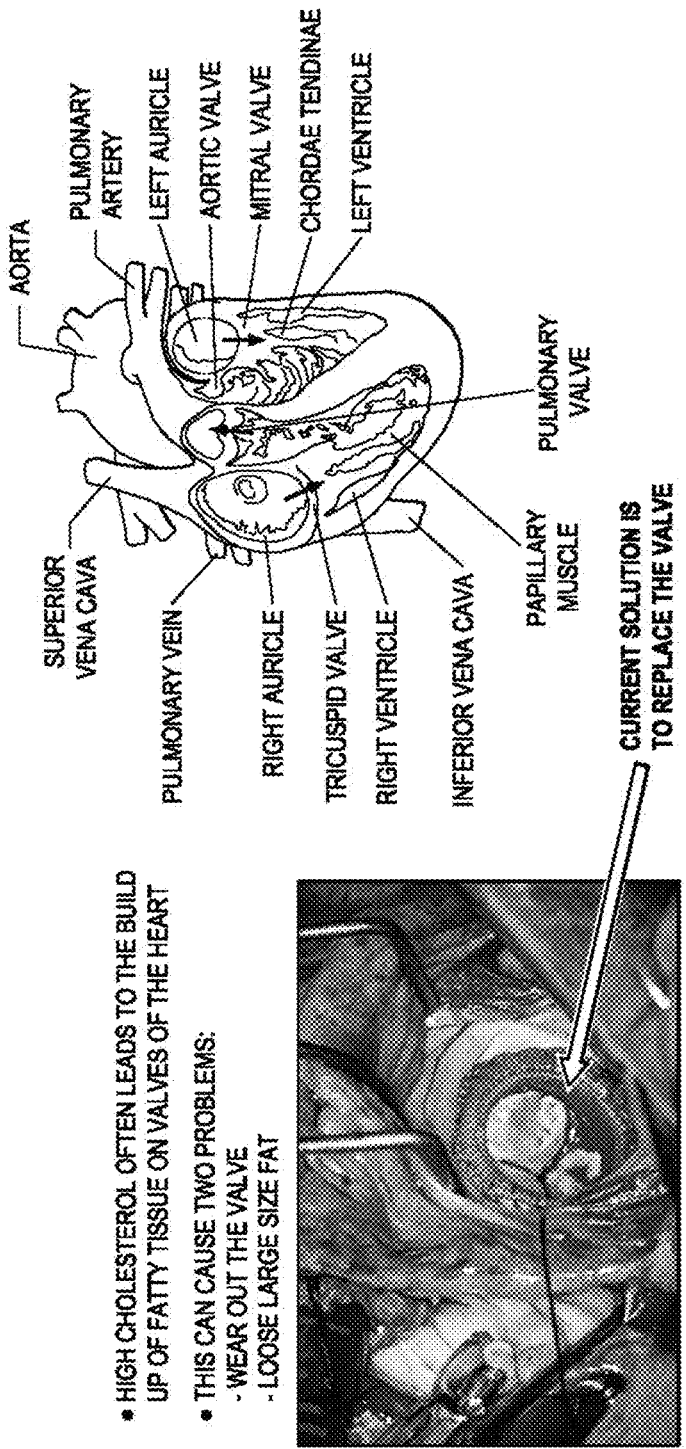
Figure 26:
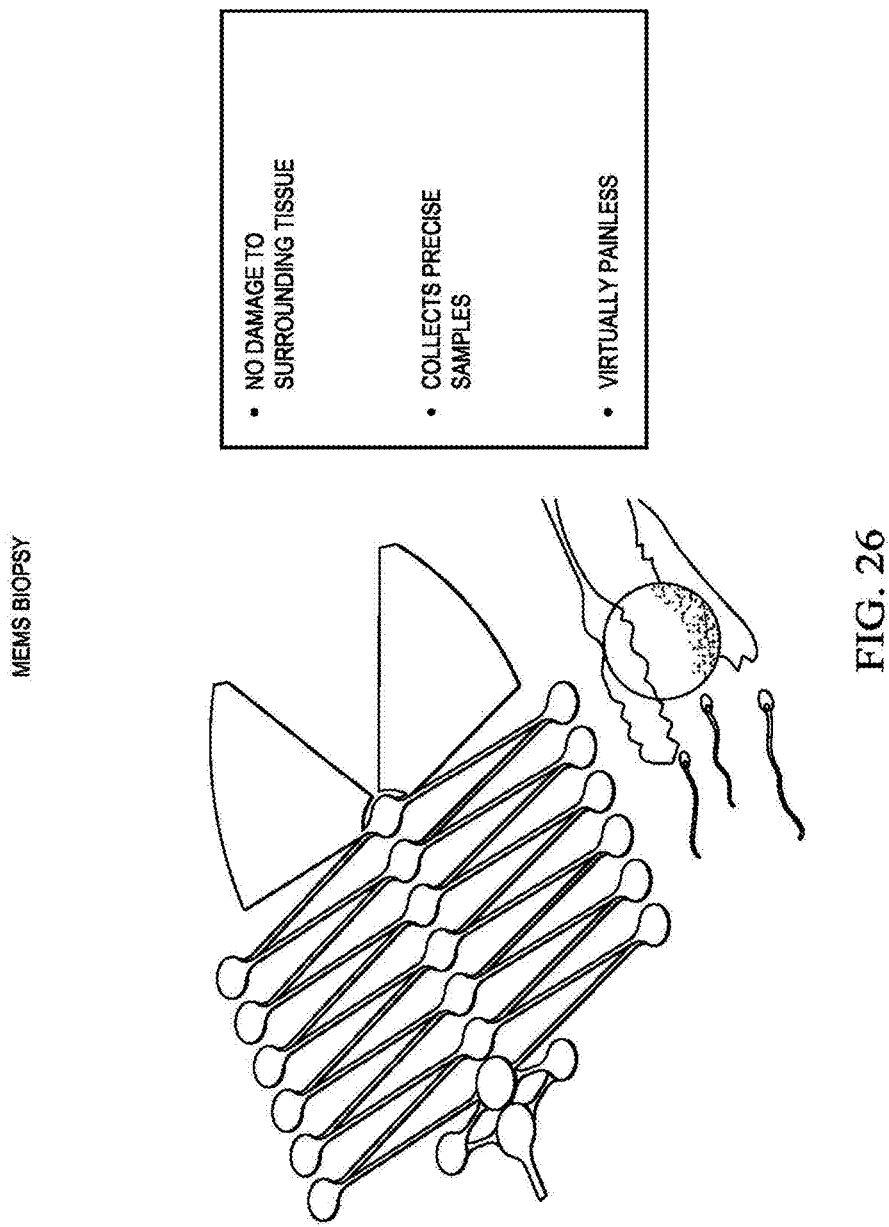
Figure 27:
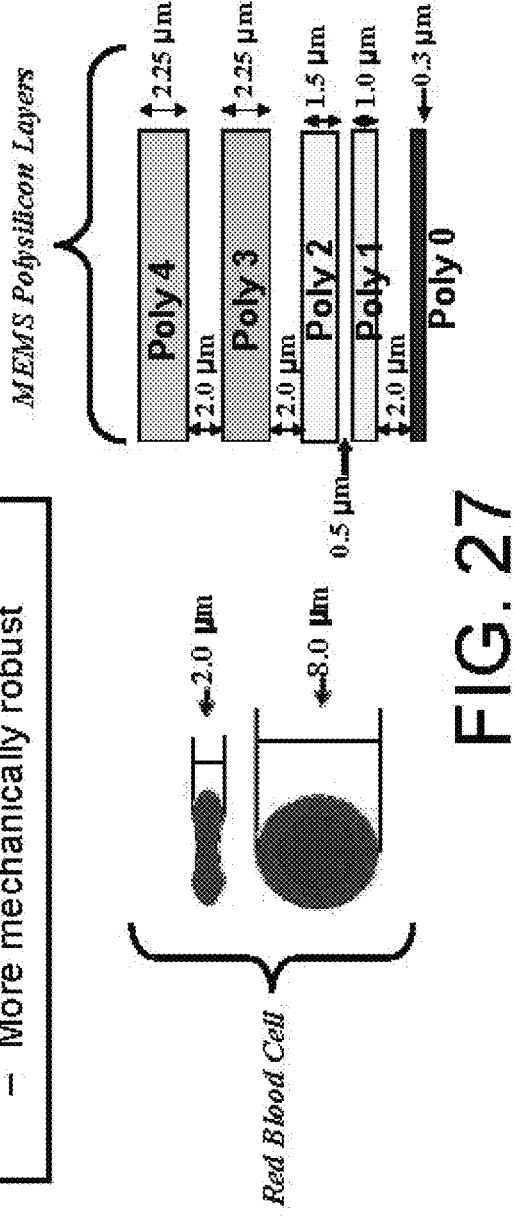
Figure 28:
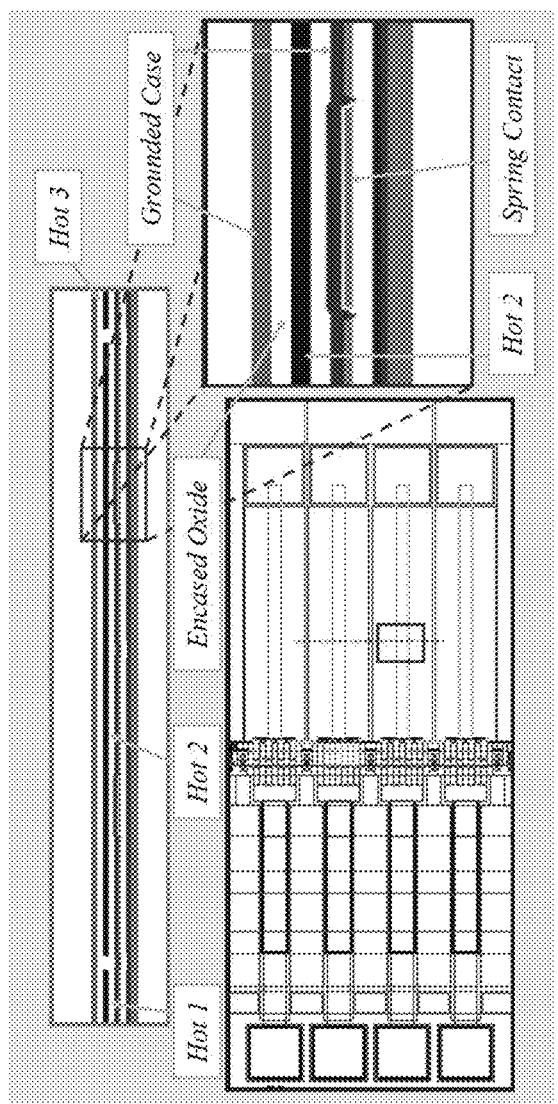
Figure 29:
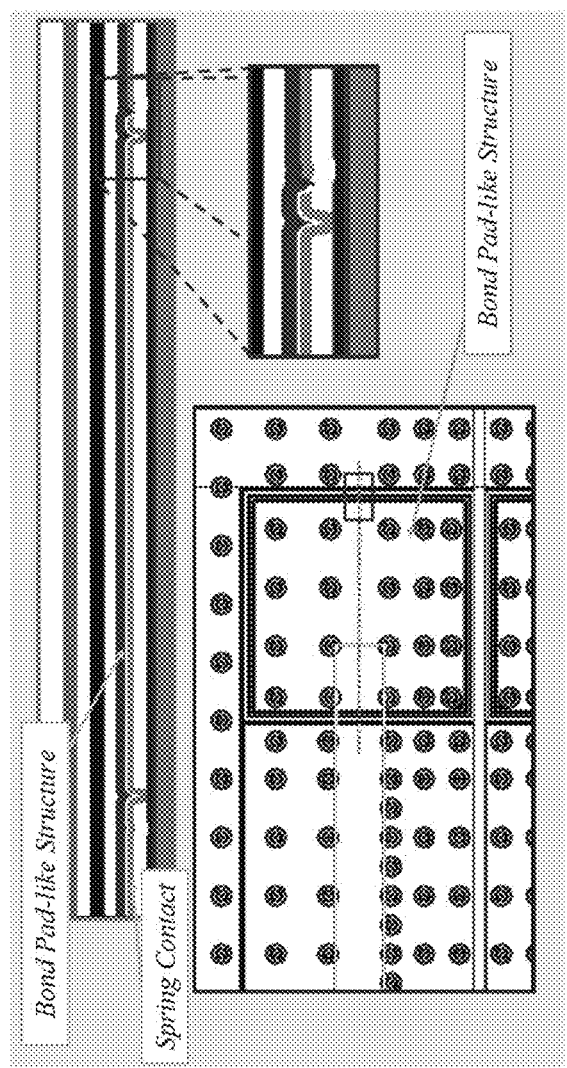
Figure 30:
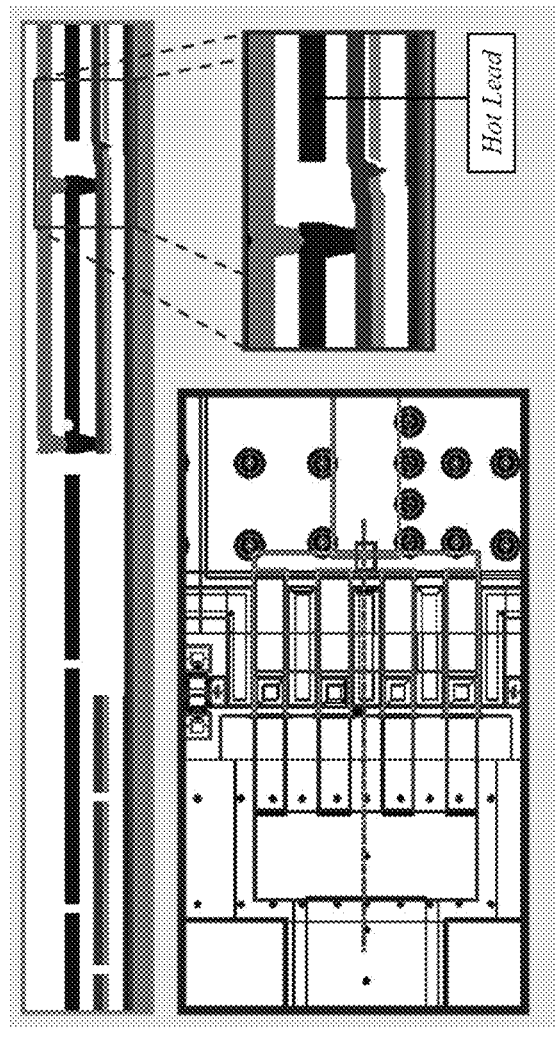
Figure 31:
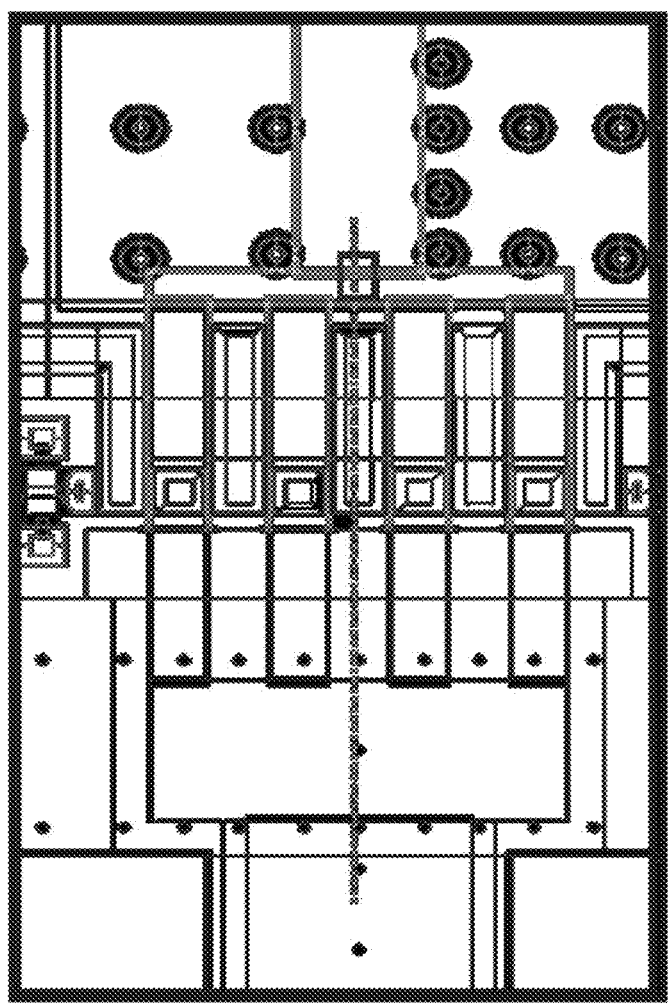
Figure 32:
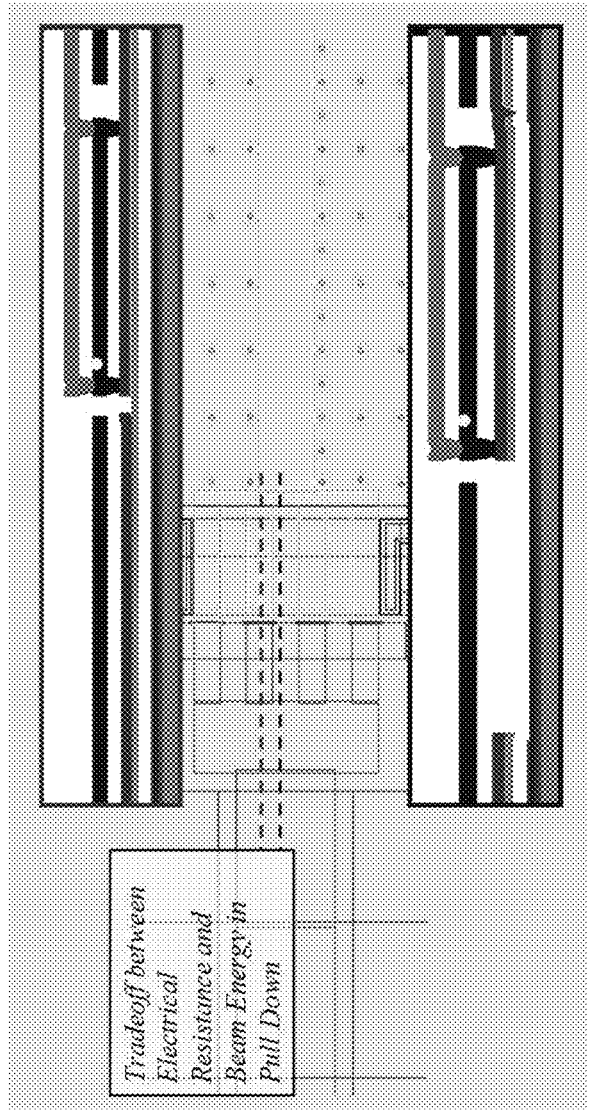
Figure 33:
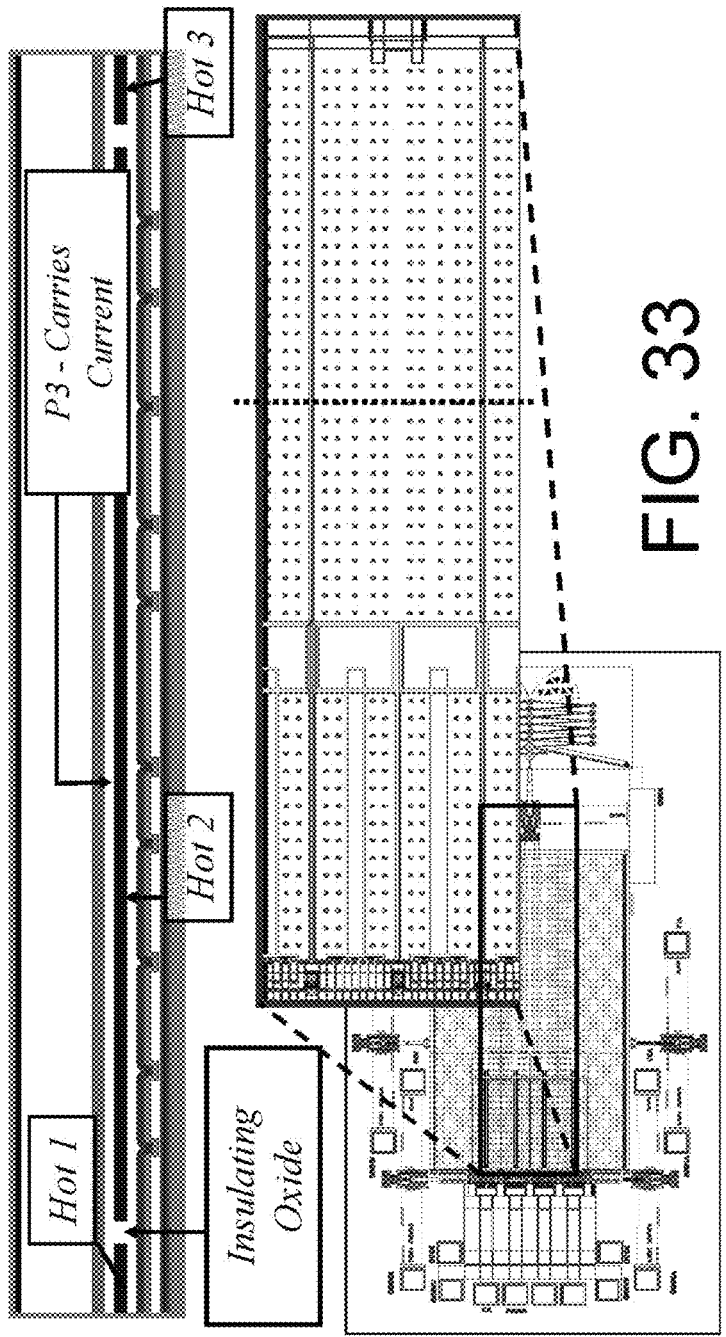
Figure 34:
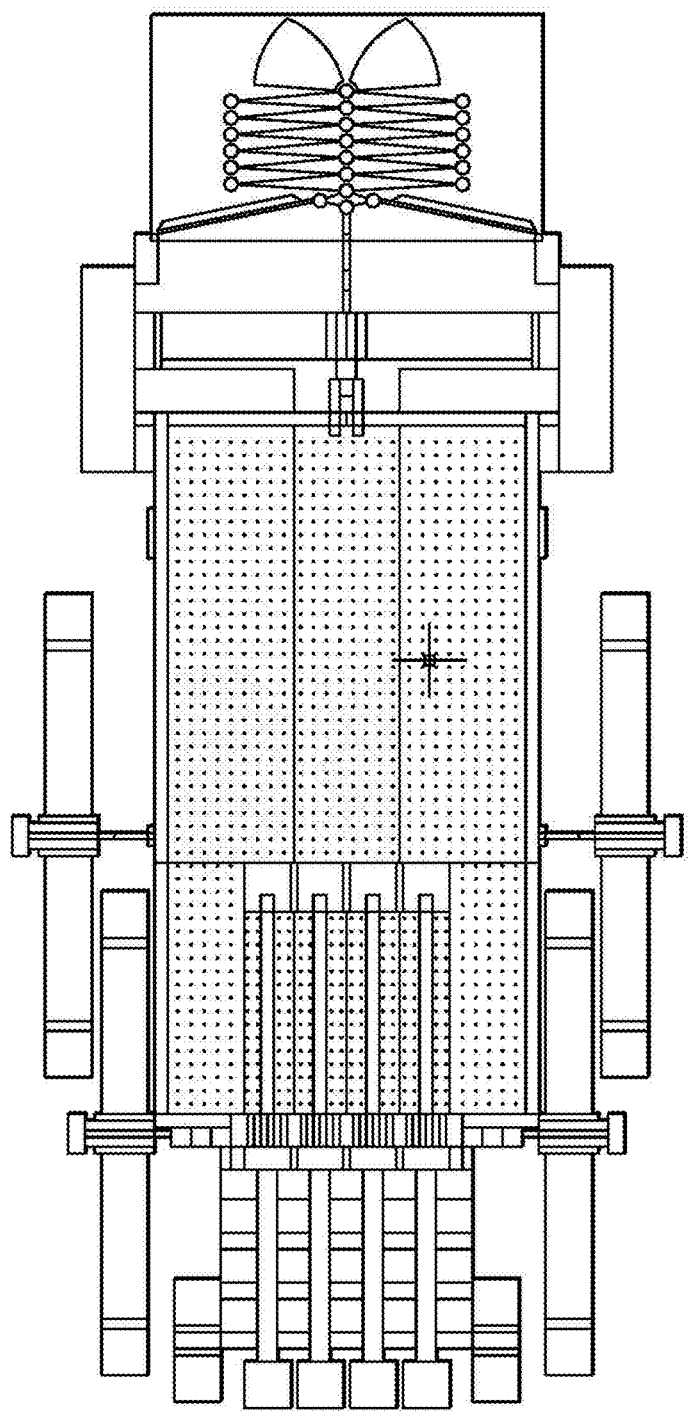
Figure 35:
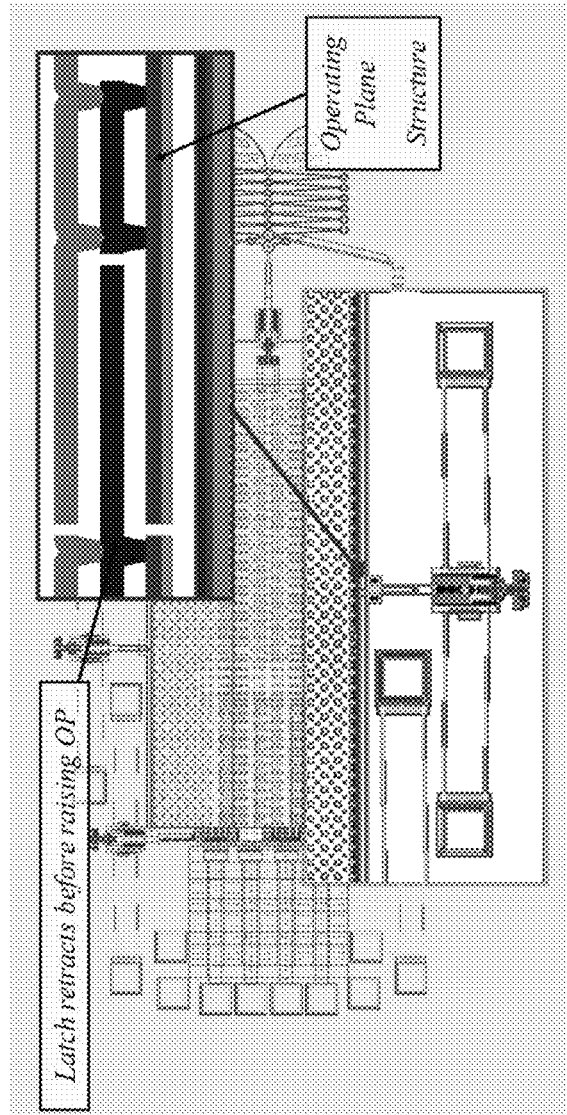
Figure 36:
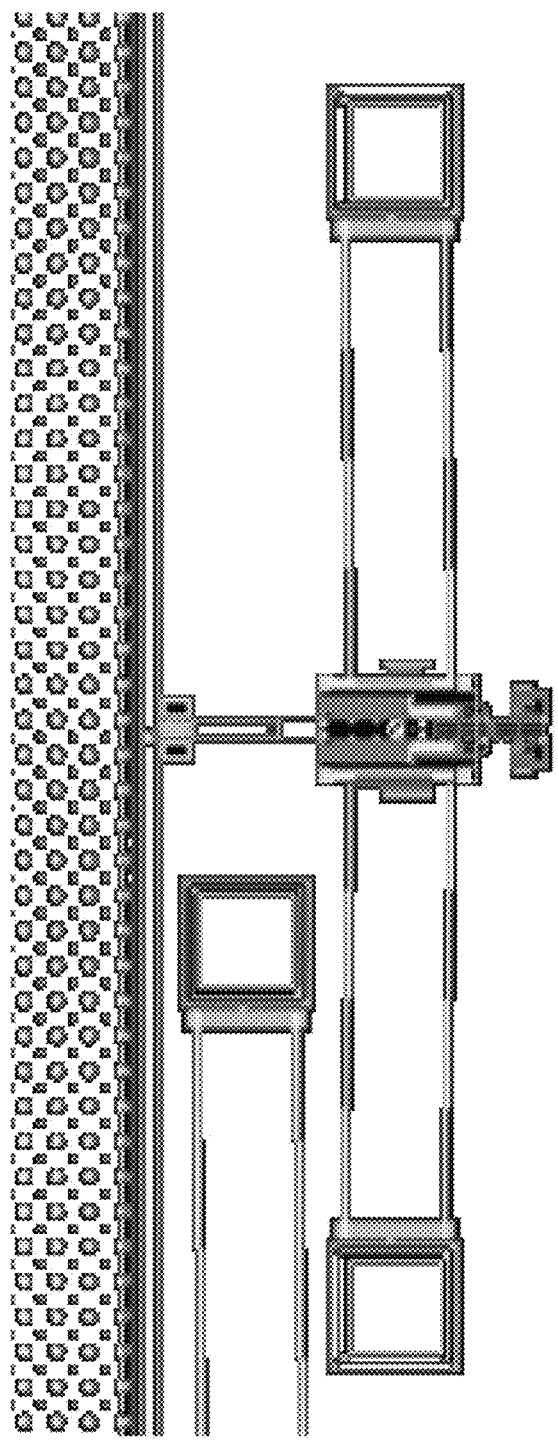
Figure 37:
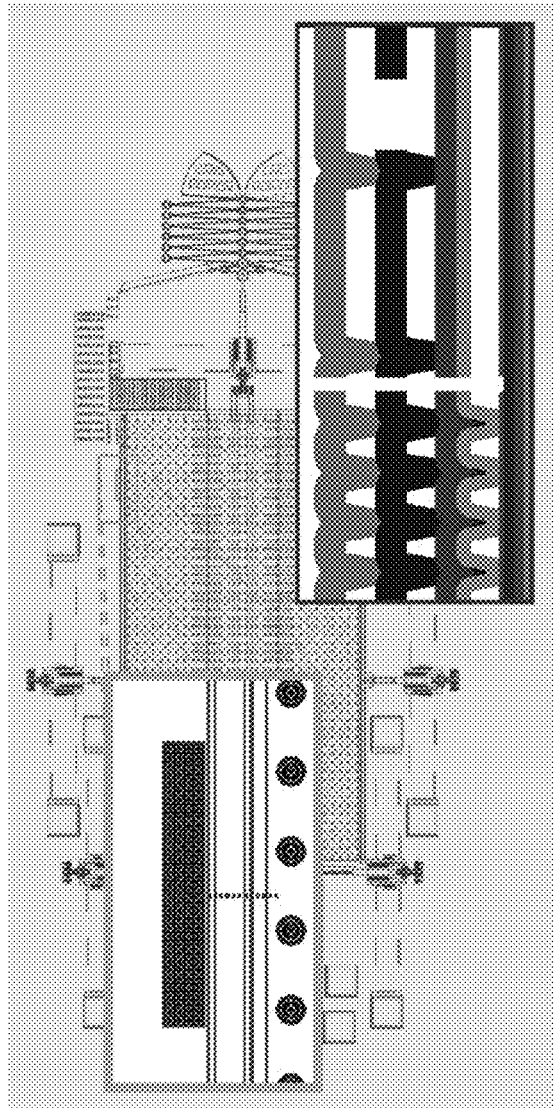
Figure 38:
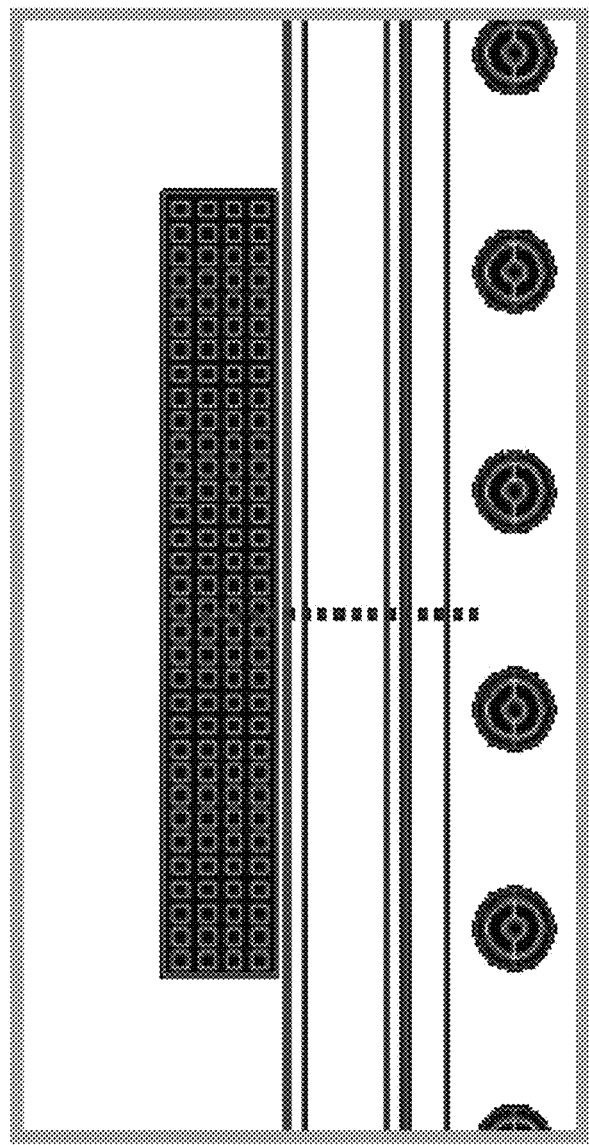
Figure 39:
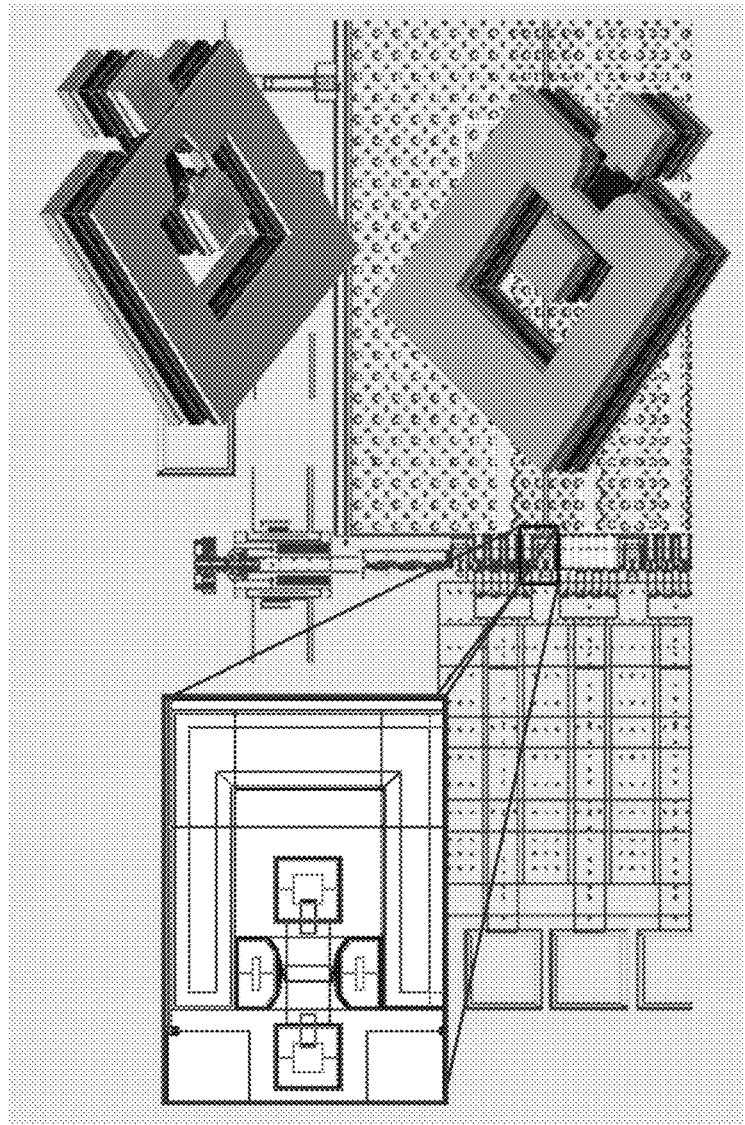
Figure 40:
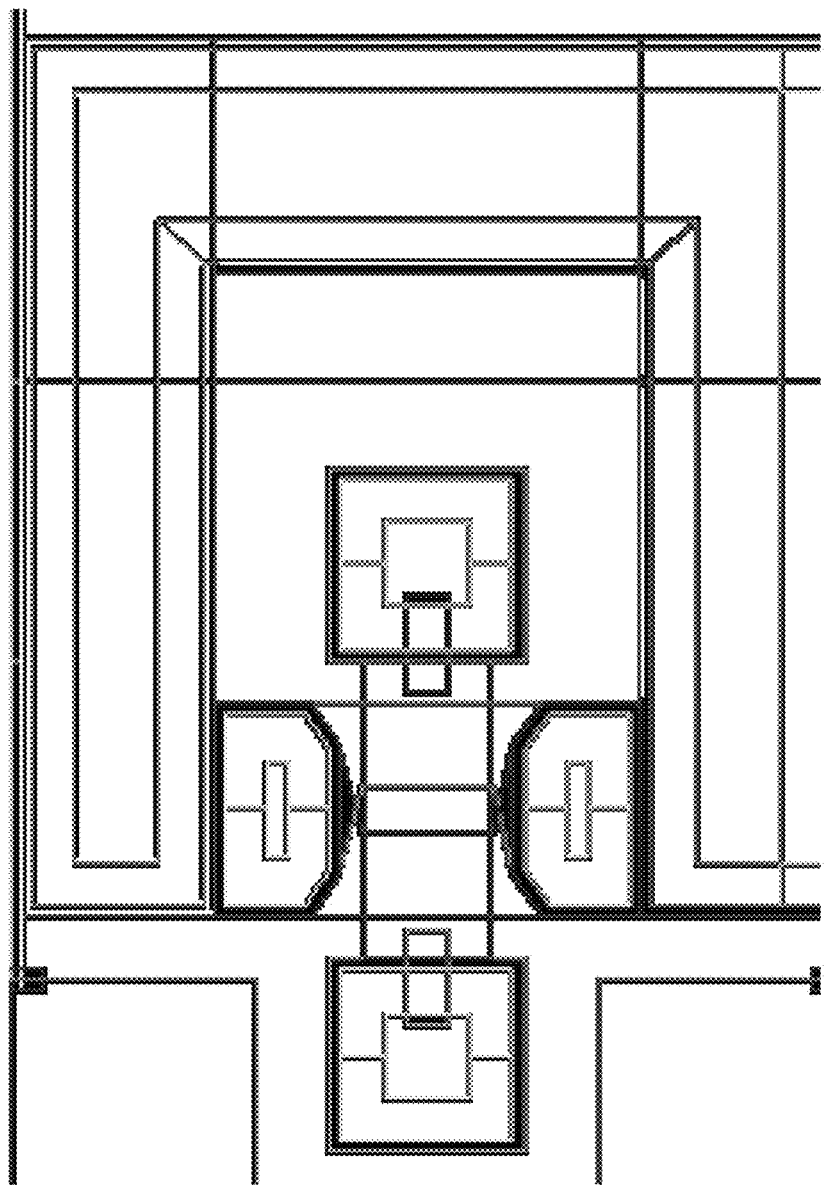
Figure 41:
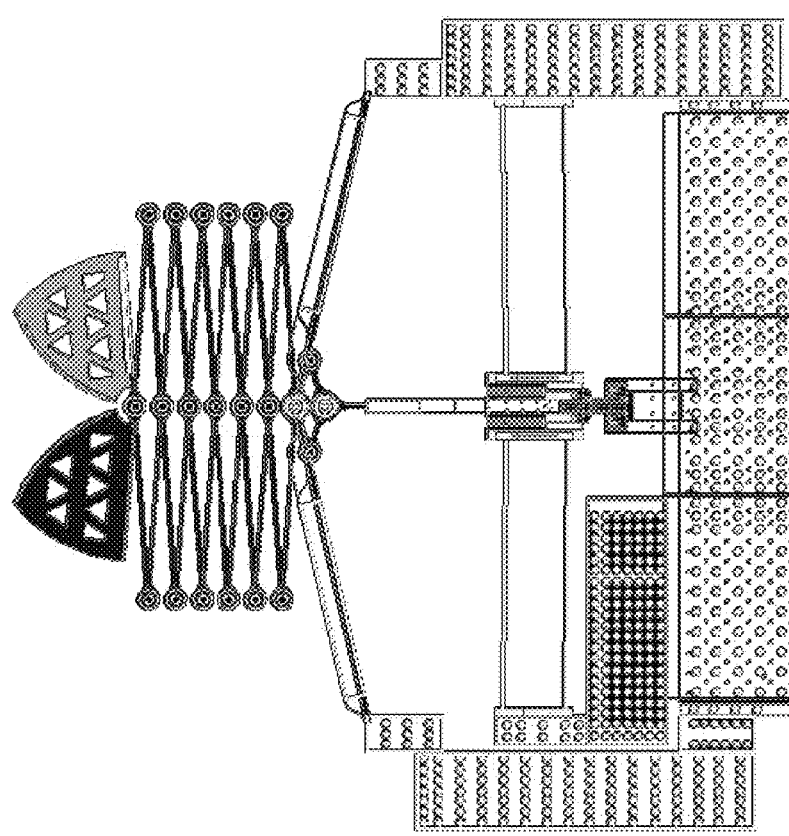
Figure 42:
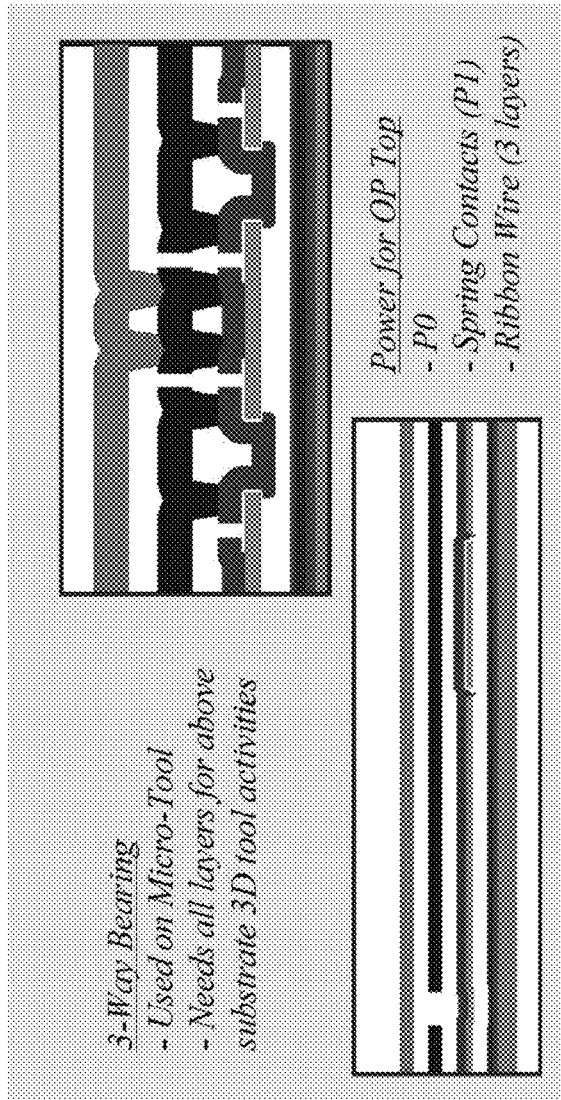
Figure 43:
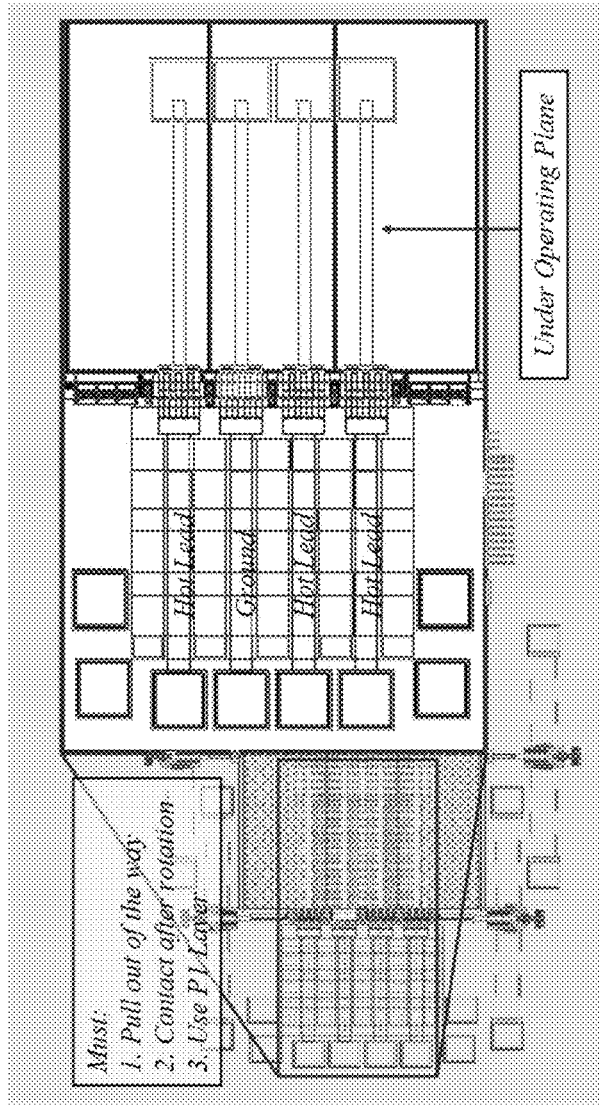
Figure 44:
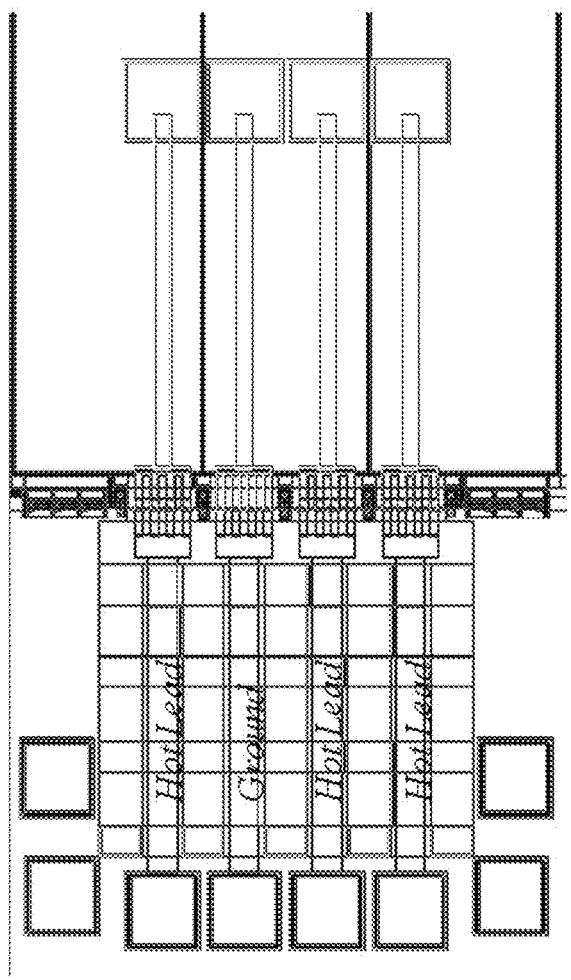
Figure 45:
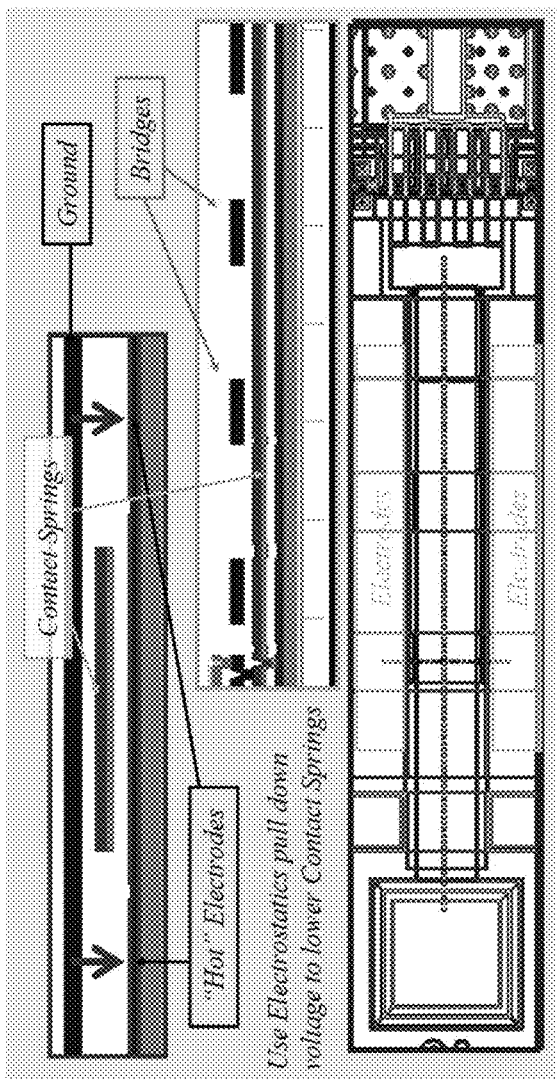
Figure 46:
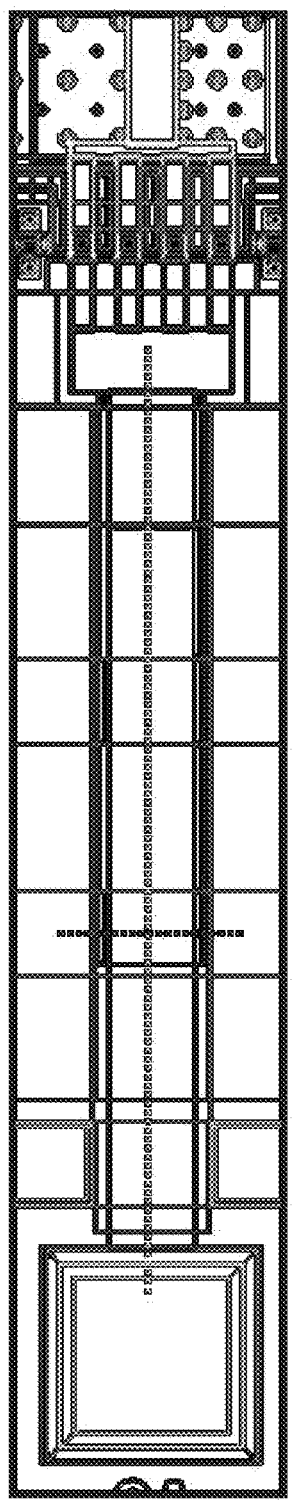
Figure 47:
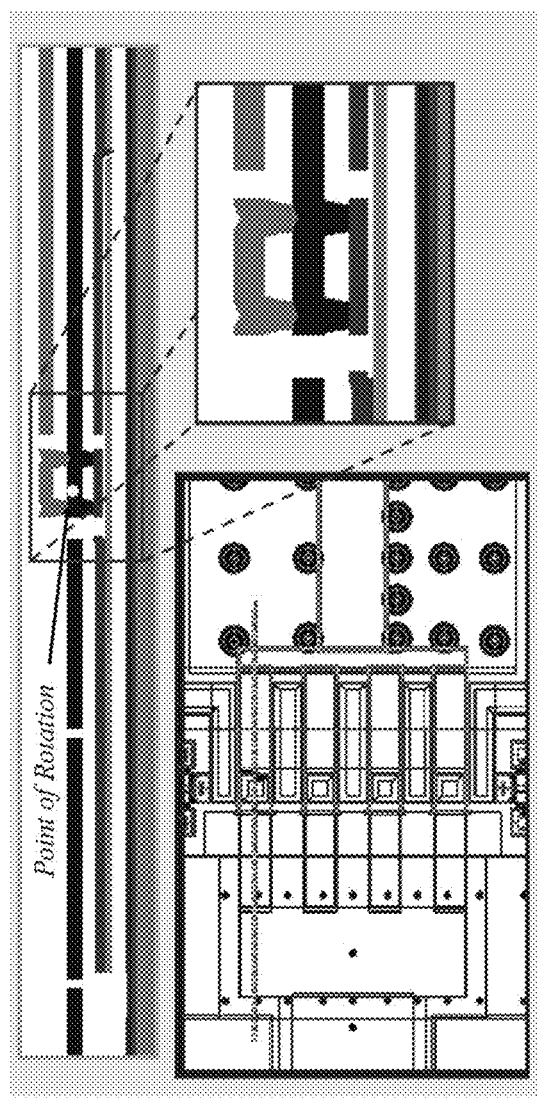
Figure 48:
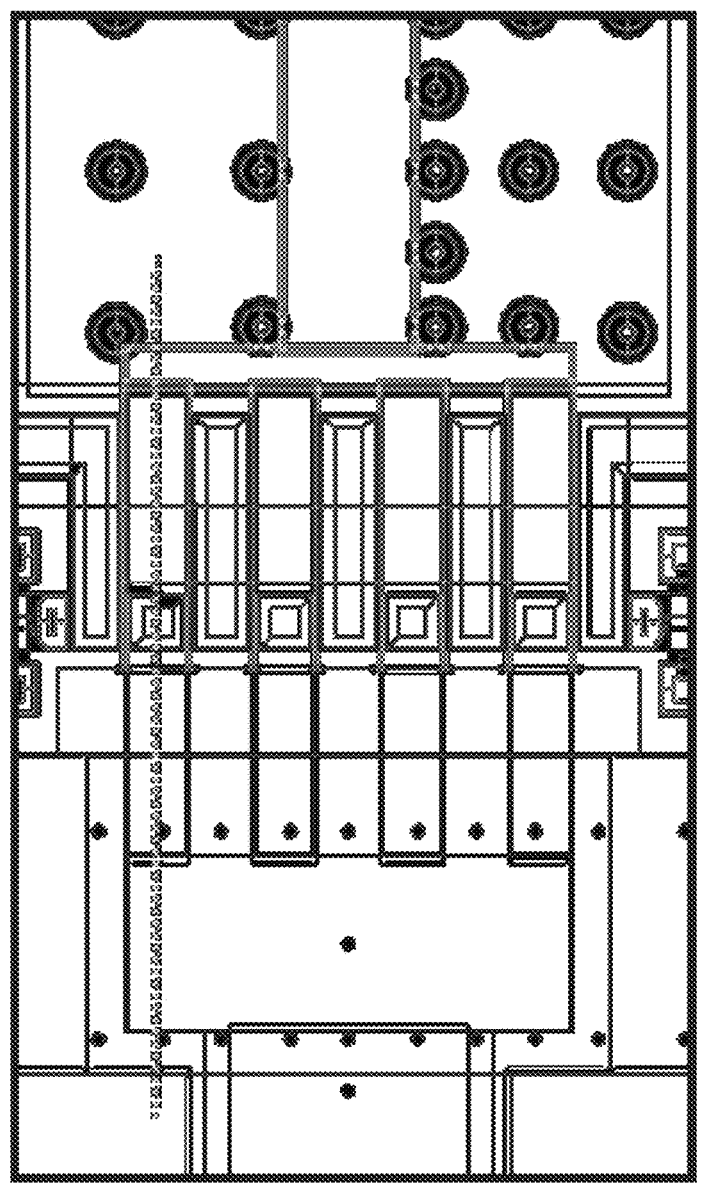
Figure 49:
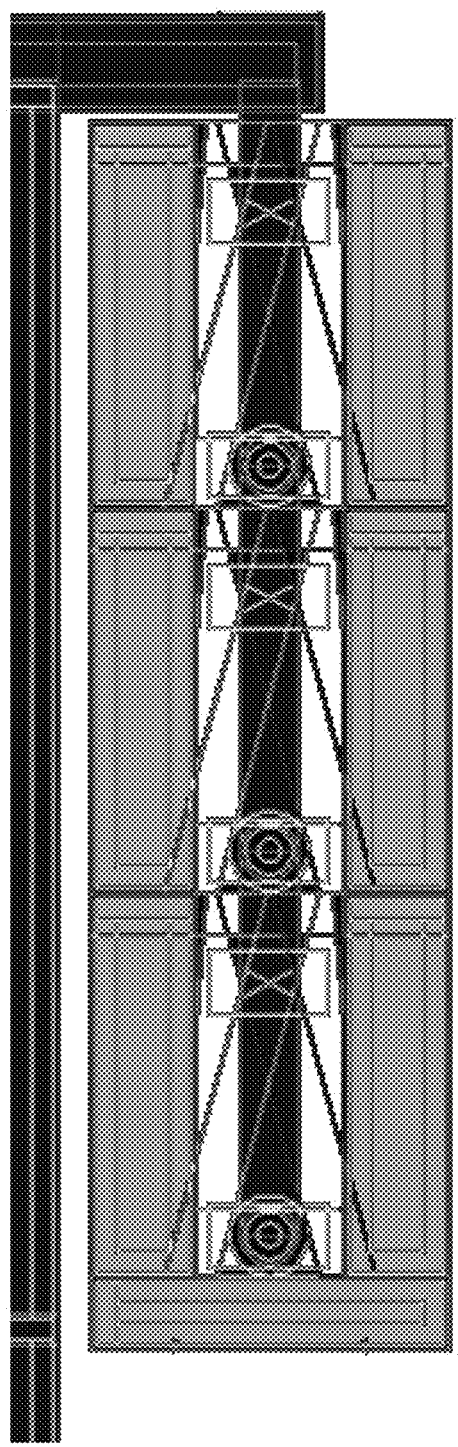

FIG. 10 illustrates biopsy tool 60. The tool was based on the shark-jaws tool and thus is very similar in shape and operation. Calculations for extension are the same as those for the shark-jaws tool because it uses an identical scissor jack, thus the maximum thermal actuator displacement of 15 μm results in a reach distance of 319 μm. Although the scissor jack system is the same, the end of the tool operates differently. The basic shape is similar to the shark-jaws in order to best fit the compacted scissor jack shape. However instead of a curved meeting of teeth, the biopsy tool 60 features straight edges that come together at one time, instead of rotating through each other. The plates that make up the head of the tool are replaced by a similarly shaped retaining device. This tool head is made by constructing a half-garage for each side of the head, using P2, P3, P4, and the Sac-Ox layers for the walls on three sides, but leaving out the P3 layer on the interior side so that material can enter into the space between the P2 and P4 layers as the two half-garages come together. This material can then be retrieved and examined.

FIGS. 11A-11D illustrate the cauterizing tool 70. There are many aspects of medicine that can benefit from micro scale tools and procedures, for the simple reason that the area of interest is almost always crowded by other sensitive organs and tissue. In order to cause the least amount of damage while affecting repairs it would seem prudent to have the least invasive tool that is capable of doing the job. Preventative care is a particular case that a tool should be able to address. The heart is the center of everything that keeps the human body functioning, and excess protein in the body can and will build up not only In veins and arteries but also on the valves of the heart. Like any well running machine these foreign inclusions will cause wear and tear. These build ups on the heart valves lead to the most frequent cause of strokes to date, the fat on the valves can break off and get pumped through that heart at a high rate of speed then jam itself up in a capillary. The back up pressure caused by this blockage can lead to a stroke. Current procedures to remove the blockages are messy, invasive, and not very reliable. Open heart surgeries, and valve replacement, are the best solutions to remove these fatty deposits. Any procedure that involves cutting the heart open and replacing a piece of it with something artificial is going to be traumatizing, and there is also a fear of the body rejecting the new part. To avoid this type of complication new methods must be developed to battle the unwanted deposits in both the arteries and veins of the body.

The MEMS micro torch is one such device that addresses the aforementioned problems. For most current high precision cutting operations doctors have used lasers. The applications of lasers in the field of medicine have aided the doctors to no end in performing precise surgical cuts and operations, but they still do not address how one reaches inside the heart without resulting in damage. With a MEMS device this could change drastically. Because of its small size and power requirements, a MEMS device would be ideal for mounting onto the front an arthroscope to give surgeons a means of interacting with and manipulating an object in teal time. Aside from the obvious advantage of causing less damage to the patient, this tool would allow for surgery to be performed in areas that are dangerous to reach. For this to be useful a precision device that could reach out above itself and do work is necessary. The same device should also be able to retract and reapproach, giving it the ability to make multiple passes and do many tasks. Because the device is small and batch fabricated, sterilization would not be necessary, simply replacing the tip of the arthroscope with a clean one is sufficient.

A tool that makes precise, measured cuts is needed for the aforementioned MEMS application. Cuts are normally made with surgical knives, but more recently the cuts are being made by either lasers or heated cutters. Heating something on this scale has proven to be both simple and reliable as evidenced by the thermal actuators. The ability to heat a rod or beam coupled with the ability to reach above the plane results in the building blocks for a micro scale precision cutting torch, but the design needs a way to retract.

To retract the jacking mechanism once it is elevated a few things must be done. First the teeth that enable the jacking system to work must be released. To accomplish this, an interlinked system involving a thermal actuator and mechanical linkages have been designed. This apparatus did require that the interim of the jacking system in both the actuator and the stationary ratcheting device be redesigned to allow for release of the teeth. Once the redesign was complete the teeth could be pulled back with a single power source, in essence giving the thermally actuated jacking system a reset button. Enabling the system to retract was the first hurdle of the design. To add reliability to the retraction and make it uniform, a spring is attached to the rear of the rod that is being extended, which will apply a spring force and retract the rod more rapidly than simply releasing the ratcheting mechanism. This was added because the device is expected to act not only in a fluid medium, but in any direction necessary, and gravity could not be relied upon to retract the rod.

For the issue of bring heat to the target area, the decision was made to utilize the same system as the beams in the thermal actuators. Since the desire is for simple heat and not a forced translation, only two side beams are truly needed. But a problem arose in the area of powering these beams. They would be moving out and back many times in even the most rudimentary surgery, and the beams themselves would be stressed constantly. To avoid excess stress on the jacking system and the beams possibly snapping under the cycling stress, the design was modified so that the beams were curved. The curved shapes acts much the same as pre-stressing on a spring, it affords the rod more length to extend without having to actually stretch the beams that are built across it. This will also reduce the required amount of force to extend the base rod in comparison to if the side beams were originally straight.

FIGS. 12-50 illustrate further information for the MEMS device.

A number of embodiments of the invention have been described. Nevertheless, it will be understood that various modifications may be made without departing from the spirit and scope of the invention. Accordingly, other embodiments are within the scope of the following claims.

What is claimed is:

1. A micro assembly, comprising:
   a substrate;
   an operating plane coupled to the substrate and movable from an in-plane position to an out-of-plane position;
   one or more electric connections providing electric power from the substrate to the operating plane in the out-of-plane position;
   a tool coupled to the operating plane; and
   the tool operable to receive electric power from the operating plane.

2. The micro assembly of claim 1, wherein the electric connection comprising electric leads between the substrate to the operating plane.

3. The micro assembly of claim 2, wherein the electric connection further comprising conductive elements in the operating plane extending from the electric leads to one or more power points for the tool, wherein the power points are at the top of the operating plane.

4. The micro assembly of claim 1, wherein the substrate comprises a chip.

5. The micro assembly of claim 1, wherein the operating plane comprises an arm.

6. The micro assembly of claim 1, wherein further comprising a tool connection connecting the tool to the operating plane.

7. The micro assembly of claim 1, wherein the tool connection providing rigidity to the tool.

8. The micro assembly of claim 1, wherein the tool is integral with the operating plane.

9. The micro assembly of claim 1, wherein the tool is detachable from the operating plane.

10. The micro assembly of claim 1, wherein the tool comprises one of pliers, cutting tool, extension device, hot knife, magnetic bead implanter gun, and biopsy tool.

11. The micro assembly of claim 1, further comprising a jacking system operable to move the operating plane from the in-plane position to the out-of-plane position.

12. The micro assembly of claim 1, further comprising a thermal actuator to convert electric power into mechanical motion for the tool.

* * * * *